United States Patent
Zocchi et al.

(10) Patent No.: US 11,032,021 B2
(45) Date of Patent: Jun. 8, 2021

(54) TREATMENT FOR IMPROVING THE USE OF DIETARY SUGAR FOR ENERGY PURPOSES

(71) Applicant: NUTRAVIS S.R.L., Genoa (IT)

(72) Inventors: Elena Zocchi, Genoa (IT); Mirko Magnone, Genoa (IT); Umberto Benatti, Genoa (IT); Giovanni Del Re, L'aquila (IT); Antonio De Flora, Genoa (IT)

(73) Assignee: NUTRAVIS S.R.L., Genoa (IT)

( * ) Notice: Subject to any disclaimer, the term of this patent is extended or adjusted under 35 U.S.C. 154(b) by 0 days.

(21) Appl. No.: 16/259,155

(22) Filed: Jan. 28, 2019

(65) Prior Publication Data
US 2019/0280799 A1  Sep. 12, 2019

Related U.S. Application Data

(63) Continuation of application No. 15/325,871, filed as application No. PCT/IB2015/055426 on Jul. 17, 2015, now abandoned.

(30) Foreign Application Priority Data

Jul. 17, 2014  (IT) .......................... TO2014A000567

(51) Int. Cl.
| | |
|---|---|
| A61K 31/19 | (2006.01) |
| A61P 3/10 | (2006.01) |
| H04J 14/06 | (2006.01) |
| A23L 33/10 | (2016.01) |
| A23L 33/00 | (2016.01) |
| A23L 33/125 | (2016.01) |
| H04B 10/80 | (2013.01) |
| H04L 7/00 | (2006.01) |
| H04L 25/08 | (2006.01) |

(52) U.S. Cl.
CPC .............. *H04J 14/06* (2013.01); *A23L 33/10* (2016.08); *A23L 33/125* (2016.08); *A23L 33/40* (2016.08); *A61K 31/19* (2013.01); *A61P 3/10* (2018.01); *H04B 10/80* (2013.01); *H04L 7/0075* (2013.01); *H04L 25/085* (2013.01)

(58) Field of Classification Search
None
See application file for complete search history.

(56) References Cited

U.S. PATENT DOCUMENTS

| | | | | |
|---|---|---|---|---|
| 7,718,699 | B1 * | 5/2010 | Broyles | A61P 25/28 514/560 |
| 2007/0184060 | A1 * | 8/2007 | Bassaganya-Riera | A61K 31/19 424/184.1 |
| 2010/0113587 | A1 | 5/2010 | Broyles et al. | |

FOREIGN PATENT DOCUMENTS

| | | |
|---|---|---|
| EP | 2511272 A1 | 10/2012 |
| WO | 2012051287 A1 | 4/2012 |

OTHER PUBLICATIONS

Merriam-Webster's Collegiate Dictionary, Tenth Edition, published by Merriam-Webster, Inc, p. 924 (Year: 1998).*
"Optimal Second- and Third-Line Therapy in Type 2 Diabetes", CADTH Optimal Use Project in Brief (Year: 2013).*
El-Shobaki et al., "Effect of Figs Fruit (Ficus carica L.) and its Leaves on Hyperglycemia in Alloxan Diabetic Rats" World Journal of Dairy and Food Sciences vol. 5 No. 1 pp. 47-57 (Year: 2010).*
Zocchi et al., "Abscisic Acid: A Novel Nutraceutical for Glycemic Control" Frontiers in Nutrition vol. 4 article 24 pp. 1-11 (Year: 2017).*
Richings et al., "Factors affecting 'Hass' avocado fruit size: Carbohydrate, abscisic acid and isoprenoid metabolism in normal and phenotypically small fruit" Physiol Plant vol. 109 pp. 81-89 (Year: 2000).*
Rao et al., "Insulin Stimulative and Anti-Oxidative Effects of Persea americana Fruit Extract on Streptozotocin Induced Hyperglycemic Rats" Journal of Medical and Biological Sciences vol. 4 issue 1 pp. 1-10 (Year: 2011).*
"Avocado—an overview" downloaded from www.sciencedirect.com (Year: 2020).*
Definition of "insulinemia" from Merriam-Webster's Medical Dictionary, downloaded from www.merriam-webster.com/medical/insulinemia (Year: 2020).*
Bassaganya-Riera et al, "Treatment of Obesity-Related Complications with Novel Classes of Naturally Occurring PPAR Agonists", Journal of Obesity, 2011, pp. 1-7.
Bassaganya-Riera et al. ,"Mechanisms of Action and Medicinal Applications of Abscisic Acid", Current Medicinal Chemistry, 2010, vol. 17, pp. 467-478.
Bruzzone, et al, "Abscisic acid is an endogenous cytokine in human granulocytes with cyclic ADP-ribose as second messenger", PNAS, 2007, vol. 104, No. 14, pp. 5759-5764.
Bruzzone, et al., "Abscisic Acid is an Endogenous Stimulator of Insulin Release from Human Pancreatic Islets with Cyclic ADP Ribose as Second Messenger", The Journal of Biological Chemistry, 2008, vol. 283, No. 47, pp. 32188-32197.
Bruzzone, et al., "The plant hormone abscisic acid increases in human plasma after hyperglycemia and stimulates glucose consumption by adipocytes and myoblasts", The FASEB Journal, 2012, vol. 26, pp. 1251-1260.

(Continued)

*Primary Examiner* — Eric Olson
(74) *Attorney, Agent, or Firm* — Silvia Salvadori, P.C.; Silvia Salvadori

(57) ABSTRACT

The invention relates to the use of a very low dosage form of abscisic acid (ABA) or an in vivo hydrolysable conjugate thereof, preferably ABA-glucosyl ester (ABA-GE), for nutracentic/therapeutic use for controlling and/or preventing hyperglycaemia and weight gain in response to sugar intake with a reduction in insulin secret and an increase in muscle performance.

15 Claims, 13 Drawing Sheets

(56) References Cited

OTHER PUBLICATIONS

Fiume et al, "Nuclear PLCs affect insulin secretion by targeting PPARy in pancreatic 13 cells", The FASEB Journal, 2012, vol. 26, pp. 1-8.

Gomez-Cadenas et al, "Direct Analysis of Abscisic Acid in Crude Plant Extracts by Liquid Chromatography-Electrosprayffandem Mass Spectrometry", Phytochemical Analysis, 2002, vol. 13, pp. 228-234.

Guiri, et al., "Abscisic acid synergizes with rosiglitazone to improve glucose tolerance and down-modulate macrophage accumulation in adipose tissue: Possible action of the cAMP/PKA/PPAR y axis", Clinical Nutrition, 2010, vol. 29, pp. 646-653.

Guiri, et al., "Dietary abscisic acid ameliorates glucose tolerance and obesity-related inflammation in db/db mice fed high-fat diets", Clinical Nutrition, 2007, vol. 26, pp. 107-116.

Jiang et al, "Long-distance signalling of abscisic acid (ABA): the factors regulating the intensity of the ABA signal", Journal of Experimental Botany, 2008, vol. 59, No. 1, pp. 37-43.

Le Barz, et al., "Abscisic Acid and Derivatives: A New Class of Molecules to Prevent Type 2 Diabetes", Journal of Nutrigenet Nutrigenomics, 2013, vol. 6, pp. 201-255, Abstract #59.

Lee et al, "Activation of Glucosidase via Stress-Induced Polymerization Rapidly Increases Active Pools of Abscisic Acid", Cell, 2006, vol. 126, pp. 1109-1120.

Lefford, "Diabetes drugs ride a bumpy road", Nature, 2013, vol. 504, p. 198.

Lin et al, "Current views on type 2 diabetes", Journal of Endocrinology, 2010, vol. 204, No. 1, pp. 1-18.

Magnone et al, "Abscisic Acid Released by Human Monocytes Activates Monocytes and Vascular Smooth Muscle Cell Responses Involved in Atherogenesis", The Journal of Biological Chemistry, vol. 284, No. 26, pp. 17808-17818. (2009).

PCT Search Report and the Written Opinion, Application No. PCT/182015/055426 filed Jul. 17, 2015, dated Nov. 9, 2015.

Scarfi et al, "Cylic ADP-Ribose-Mediated Expansion and Stimulation of Human Mesenchymal Stem Cells by the Plant Hormone Abscisic Acid", Stem Cells, 2008, vol. 26, pp. 2855-2864.

Tschope et al, "The role of co-morbidity in the selection of antidiabetic pharmacotherapy in type-2 diabetes", Cardiovascular Diabetology, 2013, vol. 12, No. 62, pp. 1-10.

* cited by examiner

TREATMENT FOR IMPROVING THE USE OF DIETARY SUGAR FOR ENERGY PURPOSES

This application is a continuation of U.S. Ser. No. 15/325,871 filed Jan. 12, 2017, which is a U.S. national stage of PCT/IB2015/055426 filed Jul. 17, 2015, which claims priority to and the benefit of Italian Application No. TO2014A000567 filed Jul. 17, 2014, the contents of which are incorporated herein by reference in their entireties.

The present invention falls within the field of therapeutical, control and prevention treatments of obesity and hyperglycemia.

More particularly, the present invention relates to the use of abscisic acid and conjugates thereof at an effective orally administered dose to improve glycemic control and the utilization of dietary sugar intake for energy purposes.

Bioactive compounds of plant origin have been used for centuries for the prevention or treatment of human diseases. Many of the more pharmacologically active molecules were first identified in plants. These bioactive molecules are normally present in plants at very low concentrations, so as to require their concentration or chemical synthesis to achieve a pharmacologically effective dose.

Compositions of plant origin are currently not available commercially for the prevention or treatment of one of the most common disorders in the developed world, i.e. glucose intolerance and its clinical manifestation, diabetes mellitus type 2 (DM2). DM2 is classified by the World Health Organization as a global epidemic, with 380 million patients worldwide (3 million only in Italy) and with an increasing incidence in developing countries (Ledford H., 2013). In 2010, 12% of global health spending was committed to the treatment of diabetes mellitus and its complications (cardiovascular disease, kidney failure, neuropathy, retinal degeneration) (Tschope D. et al., 2013).

Anti-diabetic drugs currently in use comprise diverse categories of active principles (metformin, analogues of GLP-1, inhibitors of DPP-4, insulin, glitazones, sulphonylureas, glinides), which have side effects and/or have restricted use in patients with co-morbidity, a fact quite common in diabetics (Tschope D. et al., 2013). In these patients, in fact, it is commonplace for complications such as kidney failure, heart disease or liver failure to be present which can limit the use of many of the drugs mentioned above (Tschope D. et al., 2013). In addition, insulinagogue drugs, analogues of GLP-1 and inhibitors of DPP-4, which stimulate insulin secretion in response to hyperglycemia, represent a risk factor for the maintenance of the beta-cell reservoir since they contribute to the progressive depletion of beta-cell function. Another therapeutic approach suggested for the treatment of type 2 diabetes is the pharmacological stimulation of the transcription factor peroxisome proliferator-activated receptor-$\gamma$ (PPAR-$\gamma$), for example with drugs of the thiazolidinedione class. However, the activation of PPAR-$\gamma$ induces stimulation of insulin secretion (Fiume R. et al, FASEB J, 2012) and therefore has the same disadvantage as the insulinagogue drugs.

The pathogenetic link between a diet rich in fat and carbohydrates and DM2 is currently believed to be twofold: i) inflammation of the excess adipose tissue which releases inflammatory cytokines causing insulin resistance, and ii) excessive stimulation of pancreatic beta cells, which causes depletion thereof, due to chronic hyperglycemia (Lin Y. and Sun Z., 2010).

Currently, "energizing" preparations able to stimulate peripheral consumption (muscular) of dietary glucose are not commercially available. In fact, the "energizing" preparations which are available on the market contain stimulants of the cardiovascular system (e.g. caffeine) in addition to mineral salts and sugars. Therefore, the "energizing" effect of such preparations does not involve the stimulation of energy use of glucose by the muscle. In addition, such stimulants may have undesirable or even serious side effects, particularly on the central nervous system and cardiovascular system.

2-cis, 4-trans-abscisic acid (hereinafter referred to as "ABA") is a plant hormone that regulates important physiological functions in plants, such as the response to abiotic stresses (availability of water and nutrients, UV radiation), seed dormancy and germination, and elongation of the roots. It exists in two enantiomeric forms, S-(+)- and R-(−)-ABA, both with functional effects in plants. In addition, the presence of conjugated forms of ABA in plants has been described, among which ABA-glucosyl ester (ABA-GE), an inactive ABA-conjugate, appears to be the most abundant (Jiang F. et al., 2008; Lee et al., 2006).

ABA is also present in mammalian plasma (Bruzzone S. et al., 2012), and different cell types produce and respond to ABA with activation of tissue-specific functions (Bruzzone S. et al., 2007; Scarff S. et al., 2008; Magnone M. et al., 2009). Both enantiomers of ABA (S-ABA and R-ABA) are functionally active in animal cells (Bruzzone S. et al., 2007). It has been shown that high concentrations of glucose stimulate $\beta$-pancreatic cells to release ABA, which in turn induces the release of insulin from the same (Bruzzone S. et al., 2008). In addition, the plasma concentration of ABA ([ABA]p) is increased in humans after a surfeit of glucose, indicating that ABA is in effect an endogenous human hormone (Bruzzone S. et al., 2012). In vivo studies conducted on mice rendered diabetic by a mutation in the leptin receptor indicate that dietary intake of 100 mg/kg of ABA, described by the authors as the minimum effective dose, improves glucose tolerance (Guri A. J. et al., 2007). The ameliorating effect of ABA on glycemia in vivo at the declared minimum effective dose of 100 mg/kg is attributed to the activation of the transcription factor PPAR-gamma (Bassaganya-Riera J. et al., 2007).

In order to overcome the aforementioned disadvantages of the treatments with the hypoglycemic drugs currently available, and to optimize the peripheral consumption of glucose (e.g. muscular) ingested with the diet, the present inventors have conducted experiments in order to evaluate the bioavailability of ABA and ABA-glucosyl ester (ABA-GE) when taken orally at a dose 5 logarithms less than that already used in previous studies, similar to the dose obtained on intake of a single serving of a food rich in ABA. The inventors have experimentally verified whether, at this extremely low dose, ABA has an ameliorating effect on glycemic control without however increasing insulin secretion and therefore without representing a potential harm to the population of pancreatic beta-cells, in contrast to current therapeutic strategies. A new therapeutic strategy for glycemic control that is not based on excessive beta-cell stimulation is indeed the goal pursued by researchers in the field.

The present inventors have found that the oral administration of ABA or of an in vivo hydrolysable conjugate thereof, preferably ABA-GE, at a dose comprised between 0.15 and 95 µg/day per kg of body weight of the subject, i.e. a dose which is considerably lower than that of 100 mg/kg indicated in the state of the art as the minimum effective dose, causes a reduction in glycemia after oral glucose surfeit in both rats and humans, without increasing the release of insulin, but, on the contrary, reducing the secretion thereof.

In the present description, the term "abscisic acid" or "ABA" is used to indicate both the enantiomers R-(−)-abscisic acid and S-(+)-abscisic acid and the racemic mixtures thereof.

The effect observed by the present inventors is particularly advantageous, since it allows the disadvantages of the prior art to be solved, including those related to conventional hypoglycemic therapies, which, as stated above, cause an increase in insulin secretion.

This effect is also unexpected, given that ABA induces β-pancreatic cells in vitro to release insulin after administration of high concentrations of glucose (Bruzzone S. et al., 2008).

A first aspect of the present invention is therefore ABA or in vivo hydrolysable conjugates thereof, preferably ABA-glucosyl ester (ABA-GE), for use in the therapeutic, control or prevention treatment of hyperglycemia without an increase in insulinemia, wherein said treatment comprises oral administration to a subject, human or animal, of an effective amount of ABA or conjugate thereof in a dose comprised between 0.15 and 95 µg/day per kg of body weight of the subject.

A person skilled in the art is able to adjust said effective dose depending on various factors, such as the characteristics of the subject and the specific condition to be treated. Depending on these factors, a person skilled in the art will therefore be able to select the optimum oral dose of ABA, or of an in vivo hydrolysable conjugate thereof, to be administered to the subject as hypoglycemic treatment without an increase in insulin.

In the context of the dose range indicated above, a preferred dose of ABA or of an in vivo hydrolysable conjugate thereof is comprised in the range between 0.5 and 50 µg/day per kg of body weight of the subject and a more preferred dose is comprised in the range between 1 and 10 µg/day per kg of body weight of the subject. Further preferred dose ranges are from 0.15 to 10 µg/day per kg of body weight of the subject, from 0.15 to 5 µg/day per kg of body weight of the subject, from 5 to 50 µg/day per kg of body weight of the subject, from 5 to 20 µg/day per kg of body weight of the subject, from 20 to 30 µg/day per kg of body weight of the subject, from 30 to 40 µg/day per kg of body weight of the subject and from 40 to 50 µg/day per kg of body weight of the subject.

A second aspect of the present invention is an oral dosage form of ABA or of an in vivo hydrolysable conjugate thereof, preferably ABA-glucosyl ester (ABA-GE), for use in a therapeutic, control or prevention treatment of hyperglycemia without an increase in insulinemia, wherein said dosage form is adapted for the oral administration of ABA or conjugate thereof at a daily dose comprised between 0.45 µg and 11.4 mg. Said daily dose is obtained based on a body weight of the subject, human or animal, comprised in the range of circa 3 kg to 120 kg.

Depending on various factors relating, for example, to the characteristics of the subject and to the pathology to be treated, a person skilled in the art will be able to formulate an oral dosage form suitable for the administration of an effective daily dose of ABA or of an in vivo hydrolysable conjugate thereof as a hypoglycemic treatment without increasing insulin. Said oral dosage form may also comprise suitable vehicles and/or excipients that a person skilled in the art is able to select and formulate in an appropriate manner, and also possibly further organic or inorganic active ingredients, such as substances that exert beneficial effects on the cardiovascular system, in particular substances that help reduce cholesterol and/or blood pressure.

In the context of the dose range indicated above, preference is given to a daily dose comprised between 1.5 µg and 6 mg, more preferably comprised between 3 µg and 1.2 mg. Further preferred daily dose ranges are from 0.45 µg to 1.2 mg, from 0.45 µg to 0.6 mg, from 15 µg to 6 mg, from 15 µg to 2.4 mg, from 2.4 mg to 3.6 mg, from 3.6 mg to 4.8 mg and from 4.8 mg to 6 mg.

An ABA-conjugate suitable for use in the context of the present invention is understood to mean any compound containing at least one residue of ABA and which is hydrolysable in vivo in the subject, to whom it is administered orally, so as to liberate at least one molecule of ABA. The following are indicative examples of some types of chemical bonds which, if present in the ABA-conjugates, may undergo hydrolysis and liberate ABA when taken orally:

1) anhydride bonds (with organic or inorganic acids),
2) ester bonds with alcohol or hemiacetal/ketal hydroxyl groups (e.g. primary, secondary, tertiary alcohols, mono/di/polysaccharides),
3) amide bonds (e.g. biogenic amines, amino acids).

Further characteristics of the invention are defined in the appended claims, which form an integral part of the present description.

As will be explained in detail in the section relating to the experimental part, the inventors have also observed that the aforementioned effective dose of ABA or in vivo hydrolysable conjugate thereof, described here to improve clearance of glucose in the blood of rats or humans without causing an increase in insulin secretion, can be achieved by taking the active principle (ABA or in vivo hydrolysable ABA-conjugate) either in the form of the synthetic molecule or by means of dietary intake of abundant quantities of fruit or vegetables known to be rich in ABA, such as figs (about 108 g, equal to 6-7 figs) or apricots (about 250 g, equal to 10-12 fruits) (Table 1).

Given the very low concentration of ABA in plant sources (<1 mg/g), it may be appropriate to extract and concentrate it from such plant sources to allow easy intake of an effective quantity of the active principle. Conventional methods for the extraction of ABA involve the use of potentially harmful organic solvents, even if present in small traces in the extract. The inventors have found that ABA and the conjugate thereof, preferably ABA-GE, can be extracted by a solvent-free method from plant matrices by means of extraction with supercritical $CO_2$ and extraction with supercritical $CO_2$ followed by aqueous extraction of the matrix respectively.

The experiments conducted by the present inventors have demonstrated that the aforementioned effective dose of ABA or in vivo hydrolysable conjugate thereof, in particular ABA-GE, taken orally:

(i) is highly bioavailable in humans, as demonstrated by the significant increase in the plasma concentration of ABA ([ABA]p) after taking food or plant extracts containing ABA or ABA-GE;

(ii) is able to reduce glycemia after oral glucose surfeit in both rats and humans, at an extremely low dose (in the order of units of micrograms/kg of body weight, with a consequent [ABA]p in the nanomolar range), comparable to that measured after ingestion of the same amount of the synthetic molecule;

(iii) is able to lower glycemia without increasing the release of insulin but, on the contrary, insulin levels are lower during the intake of ABA (without wishing to be bound to any theory, the inventors speculate that at this dose the in vivo mechanism of ABA in reducing glycemia is not mediated by insulin but is due to an increased uptake of glucose by muscle tissue);

(iv) is able to reduce the secretion of insulin, limiting the synthesis of triglycerides in adipose tissue resulting from the consumption of glucose, the main cause of weight gain in a diet rich in carbohydrates.

The remarkable increase in plasma concentration of ABA (ABAp) after ingesting, for example, apricots (of about 30-fold compared to baseline values, mean±SD of 4 subjects, FIG. 1B), much higher than that attributable to the increase of the same due to intake of glucose (FIG. 1B), indicates that ABA present in the fruit is readily absorbed. The bioavailability of ABA and the conjugate thereof ABA-GE, derived from foods, indicates that intake of foods rich in ABA can help control glycemia, providing exogenous ABA that can enhance the effect of the endogenous hormone. Moreover, the intake before breakfast of the effective dose of ABA (free or in its conjugated form ABA-GE) contained in plant extracts enables improvement in glucose tolerance in humans even after lunch (FIG. 3). The persistence of increased ABAp for several hours, and the resulting beneficial effects on glucose availability, can be attributed to the slow clearance from the blood of the hormone which, by binding to serum albumin, does not undergo rapid renal clearance that might be expected given its low molecular weight (264.3 Da).

The fact that the observed lowering of glycemia on ingesting this effective dose of ABA (free or in its conjugated form ABA-GE) is not due to an increased release of insulin was not predictable from the prior art where, in contrast, the stimulatory effect of synthetic ABA on insulin release from isolated β-pancreatic cells in vitro was observed (Bruzzone S. et al., 2008). Without wishing to be bound to any theory, the inventors believe that the in vivo effect generated by this effective dose of ABA may be due to a different timing of the effectiveness of ABA on these types of cells, in particular in the stimulation of glucose transport that can precede and/or override the effect on stimulating the release of insulin. Furthermore, in vivo, human cells expressing GLUT4 can be more sensitive to the effects of ABA than β-pancreatic cells. In vitro, human β-pancreatic cells and rat myoblasts were similarly sensitive to the stimulatory effect of nanomolar ABA on the release of insulin and glucose uptake respectively (Bruzzone S. et al., 2008; Bruzzone S. et al., 2012): however, in vitro experiments on isolated cells from different species, while providing useful information regarding the possible biological effect of a molecule, are scarcely predictive of the in vivo behaviour of the same molecule.

The inventors believe that the daily intake of the aforementioned effective dose of ABA or ABA-GE is effective in both healthy subjects and in diabetic or pre-diabetic patients.

In healthy subjects, the daily intake of ABA allows a reduction in the 24-hour AUC of blood glucose without increasing insulinemia, prolonging β-pancreatic cell functionality and reducing insulin-dependent synthesis of triglycerides in adipose tissue. The latter effect contributes to the optimal maintenance of body weight (BW). Patients with type 1 diabetes (T1D) benefit from the effects of insulin-independent glycemic reduction generated by the dose of ABA or ABA-GE. Finally, in pre-diabetic subjects or patients suffering from diabetes mellitus type 2 (DM2), the latter being insulin resistant, drug therapy with hypoglycemic secretagogues accelerates the depletion of the insulin reserves of the β-cells by stimulating an excessive release of insulin. The effective amount of ABA or ABA-GE described here can, on the contrary, reduce the stimulation of the β-cells to release insulin in response to hyperglycemia, prolonging the survival and function of the same and decreasing the synthesis of insulin-mediated triglycerides in the adipose tissue, thus reducing the BW.

In the light of these considerations and of studies conducted by the present inventors that will be illustrated in greater detail below, embodiments of the present invention include the use of the aforementioned effective dose of ABA or in vivo hydrolysable ABA-conjugate for reducing glycemia, for improving glucose tolerance without increasing insulin secretion, for improving muscle glucose adsorption and consequently muscle performance and endurance, for reducing insulin secretion or for replacing insulin in the control of glycemia in normal subjects and diabetics and for reducing the synthesis of fat (triglycerides) and deposition thereof after intake of carbohydrates.

Further embodiments of the present invention include the use of ABA or in vivo hydrolysable ABA-conjugate in the preparation of human or animal food rich in carbohydrates characterized by a high glycemic load, by means of addition to such foods of the aforementioned effective dose of ABA or conjugate thereof, and also the use of ABA or conjugate thereof in the formulation of supplements able to promote muscle uptake of glucose, such as energizing beverages containing sugars in combination with the aforementioned effective dose of ABA or in vivo hydrolysable conjugate thereof.

In all these embodiments of the invention, ABA or the ABA-conjugate is used as a synthetic molecule or, alternatively, as a plant extract enriched in ABA and/or conjugate thereof, preferably obtained by extraction using supercritical $CO_2$ or aqueous extraction.

The following experimental part is provided solely for illustrative purposes and is not intended to limit in any way the scope of the present invention as defined by the appended claims.

EXPERIMENTAL PART

Materials and Methods

Determination of ABA in Different Foods

Figure 1A:
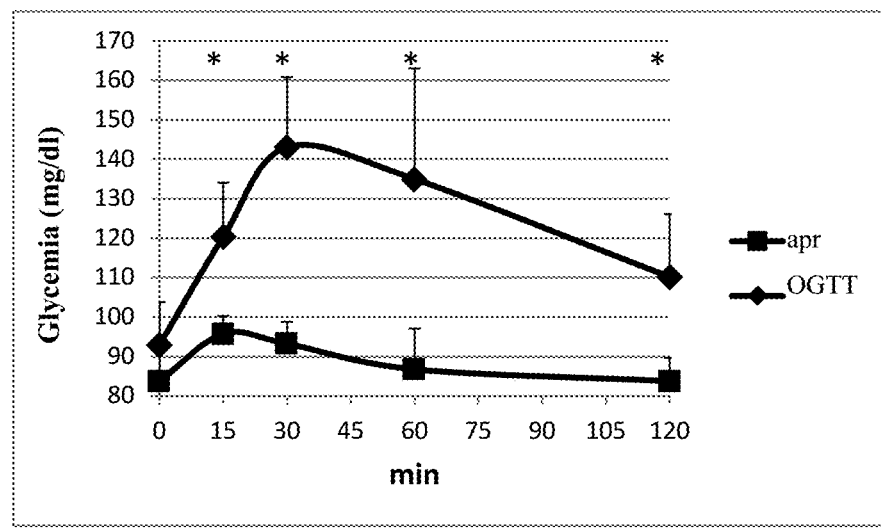
FIG. 1A shows the changes of glycemia after intake of apricots (apr) or after oral glucose load (OGTT)

Two grams each (wet weight) of the fruits and vegetables listed in Table 1 were homogenized in 2 ml of water, sonicated on ice to 600 W for 10 seconds and added with 4 volumes distilled methanol. To determine the ABA content in the standard breakfast and lunch, a tenth of the amount of each component listed in Table 4 was mixed and homogenized. A 2 g-aliquot of homogenate was added to 4 volumes of distilled methanol. A small amount of [3H]-ABA ($3 \times 10^3$ cpm) was added to each sample as an internal standard and all extracts were kept at $-20°$ C. for 24-48 hours before further processing. After centrifugation (2000×g for 10 minutes), the supernatants were dried in a Rotovapor, the extracts were taken up in 3 ml deionized water, the pH was brought to between 2.5-2.6 with 0.1% trifluoroacetic acid and subjected to 3 successive extractions with 2 volumes each of ether. The ether was evaporated in a Rotovapor and the final extracts were again taken up in 250 µl deionized water. Samples were then injected into an analytical column Atlantis DC18 (Waters, Milford, Mass.) (3.9×150 mm; particle size 5 micrometers). Buffer A was water containing 0.01% trifluoroacetic acid (TFA), buffer B consisted of 80% acetonitrile in water containing 0.01% TFA, and the flow rate was 0.8 ml/min. The gradient was from 100% A to 100% B in 30 min. Fractions were collected every 30 sec: radioactives fractions were dried and redissolved in 11 µl of a solution made of 90% buffer A and 10% buffer B of the HPLC-coupled to mass spectrometry (HPLC-MS) (see below), and [$^2$H6]-ABA was added as internal standard. Two microliters were counted to calculate the extraction yield, the rest was subjected to capillary chromatography. The samples were analyzed using the Agilent 1100 system for capillary chromatography, equipped with a diode array detector coupled to a mass spectrometer Agilent 1100 series LC/MSD Trap, equipped with an electrospray source with orthogonal geometry analyzer and ion trap. The HPLC separation was performed on a Waters Atlantis DC18 column (150×1 mm; particle size, 3 microns) at a flow rate of 30 µl/min; Buffer A was 1% vol/vol of acetic acid in water, buffer B was 90% acetonitrile and 10% buffer A; the gradient was as follow: 0 to 3 min 100% A and from 3 to 35 min, increasing linearly, up to 100% B. The system of detection was set at a wavelength of 254 nm. MS and MS/MS spectra were acquired in negative ion mode in the range 50-300 m/z. The presence of fragments at 153 and 219 Da (Gomez-Cadenas A. et al., 2002) unequivocally identified the elution peak as 2-cis, 4-trans-ABA. The concentration of ABA in the extracts was calculated from the area of its HPLC peak taking into account: (i) the percentage of recovery, evaluated with the radioactive tracer, (ii) the efficiency of ionization, evaluated with the internal standard of deuterated ABA added before HPLC-MS analysis, and (iii) a calibration curve, obtained with known amounts of ABA, injected separately.

Human Volunteers

Six healthy volunteers (3 males and 3 females, aged 30-65, body mass index, BMI, ranging between 21-32 kg/m$^2$) underwent an oral glucose tolerance test (OGTT). Six subjects participated in the experiments with the supercritical plant extract containing endogenous ABA: 3 males (30, 36 and 45 years; BMI between 20.2 and 25.6 kg/m$^2$ respectively named #1, #2 and #3) and 3 females (aged 52, 42 and 31; BMI between 21 and 22 kg/m$^2$ respectively referred to as #4, #5 and #6). None of the subjects was following any dietary restrictions or special diet at the time of trial. Four subjects (#1, #2, #5 and #6) took part in the experiment with the apricots. Three subjects underwent an OGTT in the presence or absence of a supercritical plant extract containing an appropriate dose of ABA (#1, #2 and #3) and three subjects were subjected to the standard breakfast and lunch, with or without an aqueous fruit extract containing an appropriate dose of ABA (#1, #2 and #4). At least one week elapsed between two subsequent experiments on the same subject.

Determination of Plasma Concentrations of Glucose, Insulin and ABA

Heparinized samples of human blood (5 ml), were centrifuged immediately after collection at 2000×g for 10 min. Two ml of plasma were immediately extracted with 4 volumes of distilled methanol for the determination of [ABA] p. The residual plasma was stored at $-20°$ C. for 10-14 days and then used for measurements of glucose, insulin and ABA. All measurements were performed in duplicate on each sample obtained from the same subject. The plasma glucose concentration was measured by an enzymatic method (Randox Laboratories, Crumlin, UK). The values obtained were comparable (SD 3%) with those measured at the same time with a capillary blood glucometer (Bayer). The plasma insulin concentration was determined by immunoradiometric assay (Immunotech, Prague, Czech Republic), with an intra- and inter-assay sensitivity of 0.5 ng/ml, ≤4.3% and ≤3, 4%, respectively. The extraction of ABA and the determination of its concentration by HPLC-MS were performed as described in (Bruzzone S. et al., 2012). For the determination of blood glucose in rats, blood samples were taken from the tail vein of anesthetized animals and blood glucose was measured with a glucometer (Bayer). The quantification of insulin on the same animals, was carried out by sampling blood from the orbital sinus, immediately adding heparin and subjecting each sample to centrifugation at 22000×g for 30 sec: aliquots of plasma were stored at $-20°$ C. The plasma insulin concentration was determined with an ELISA kit (Bertin-Pharma, Montigny, France).

Supercritical $CO_2$ Extraction of ABA from a Vegetable Matrix

Fresh plant samples were dried in a heater at 50° C. for different times in order to achieve the desired percentage of moisture. Three hundred and fifty g of the dried sample were placed into the extraction chamber (500 ml) of the apparatus for the extraction in supercritical fluid (SFE). The supercritical $CO_2$ extraction ($CO_2$ flow rate 5 grams/min) was carried out at 250 bar and 40° C. with dynamic extraction. The extract, obtained in a liquid form, was collected in a glass container, directly connected with the apparatus of extraction. The amount of ABA in the supercritical extracts (SE) was measured with a specific enzyme immunoassay (ELISA, Agdia, USA) and confirmed by HPLC-MS analysis.

Aqueous ABA and ABA-GE Extraction from a Plant Matrix

Plant samples, recovered from the extraction chamber after SFE or fully dried and not subjected to SFE, were weighed and rehydrated for 30 min in a beaker containing ultra pure water (0.5 ml water/g sample) at room temperature. After rehydration, samples were filtered under vacuum to recover the adsorbed water. Rehydration and filtration were repeated two more times on the same sample. To hydrolyze ABA-GE and release free ABA, an aliquot of the aqueous extract was subjected to alkaline hydrolysis, as described in (Bruzzone S. et al., 2007). The amount of ABA contained in the aqueous extract, subjected or not to alkaline hydrolysis, was measured using a specific enzymatic immunoassay (ELISA, Agdia, USA) and confirmed by HPLC-MS analysis. The amount of ABA-GE present in the aqueous extract was calculated from the area of the chromatographic peak of ABA generated by alkaline hydrolysis of the HPLC fraction of the extract containing ABA-GE. This fraction was identified through the following chromatographic and mass spectrometry criteria: 1) co-elution in HPLC with synthetic ABA-GE (standard), 2) identity of the mass of the molecular ion with the standard, and 3) identity of the mass-mass spectrum with the standard. The amount of free ABA and ABA-GE taken from volunteers with the plant aqueous extract is defined as "total ABA": free ABA was 45±4% of total ABA (n=5).

Oral Glucose Tolerance Test (OGTT) in Rats

Wistar male rats (obtained from Charles River, Milan, Italy), age between 9 and 13 weeks, were divided into two groups (12 animals per group) and fasted for 17 hours. After mild sedation with diazepam, 1 g/kg BW of glucose was administered by gavage in about 300-400 µl of aqueous solution, containing or not 1 µg/Kg BW of synthetic ABA, or the same dose of ABA or ABA-GE endogenously present in a supercritical or water plant extract. Immediately after gavage, rats were anesthetized with xylazine and ketamine. Blood glucose was measured with a glucometer on blood taken from the tail vein immediately before gavage (time zero) and 15, 30 and 60 minutes after gavage. Each measurement was performed in duplicate.

OGTT in Humans

The OGTT were performed in the morning after overnight fasting. Six volunteers were subjected to a standard OGTT (without ABA). The three subjects who underwent an OGTT in the presence or absence of a supercritical extract containing endogenous ABA performed two tests each, one with glucose only (OGTT no extr), i.e. a standard OGTT, the other one with the same amount of glucose in the presence of 1 µg/Kg BW of ABA endogenously present in the supercritical extract (OGTT+extr). The two tests were performed at a one week interval from each other: subjects #1 and #2 underwent the OGTT+extr first, while subject #3 underwent the OGTT no extr first. All subjects drank 150 ml of a solution of 50% glucose (Sclavo Diagnostics International, Siena, Italy) in 5 min. Blood sampling was performed immediately before intake of glucose (time zero) and after 30, 60 and 120 min. The blood samples were treated as previously described for the determination of the concentrations of glucose, insulin and ABA.

Experimental Breakfast and Lunch

After overnight fasting, three volunteers consumed a standard breakfast followed four hours later by a standard lunch (see Table 4 for the composition). Each subject underwent two experiments, one without extract (no extr), the other with an aqueous extract containing an amount of endogenous ABA such as to yield a dose of 1 µg/Kg BW of ABA. Subjects #1 and #2 underwent the experiment without extract first, while subject #4 underwent the experiment with the extract first. Blood samples were carried out immediately before breakfast (time zero) and after 30, 60, 120, 240 and 360 min. Blood samples (5 ml) were collected in heparin and treated as previously described for the measurement of plasma concentrations of ABA, glucose and insulin.

The Daily Oral Intake of Synthetic ABA at a Dose of 1 µg/Kg Reduces the Weight Gain Induced by Chronic High-Dose Glucose (1 g/Kg) in Mice Five week-old female CD1 mice (outbread) (9 per group) were administered glucose in the drinking water, without (controls) or with the addition of synthetic ABA. To achieve the required daily dose of glucose (1 g/kg BW) and of ABA (1 µg/Kg BW) the daily volume of water drank by the animals used for the test was preliminary established. Based on this volume (5 ml/day), and taking into account an average weight of the mice of 30 grams, the water administered to the animals, contained 0,006 g/ml of glucose and 0.006 µg/ml ABA. The weight control was performed after 12 weeks of treatment on the two groups of animals fasted for 17 hours before measurement of the weight. The reason for using female CD1 for this test was that they show a natural predisposition to accumulation of adipose tissue that is not found, instead, in males of the same strain.

The Daily Oral Intake of Synthetic ABA at a Dose of 1 µg/Kg Improves Muscle Performance in Mice Male CD1 mice (outbread) (8 per group) were administered glucose with the drinking water without (controls) or with the addition of synthetic ABA. The concentrations of glucose and of ABA in water were calculated considering the average daily volume drank by each mice so as to reach a dose of 1 g/Kg BW and 1 µg/Kg BW of ABA. After 12 weeks of treatment the mice (average weight 45.1 and 43.3 grams for the animals treated with glucose and glucose+ABA, respectively) were kept 12 hours in two separate cages, each equipped with a wheel connected to a digital odometer measuring the total distance traveled on the wheel and the time of rotation of the wheel. The tests were performed during the night time on animals with freely available food and water containing glucose alone (controls) or glucose+ABA. The reason for using male CD1 mice for this experiment is their natural predisposition to develop more muscle mass compared to females from the same strain.

Results

ABA Content in Some Vegetable Sources

Extracts from different types of fruits and vegetables typical of the Western diet were prepared and the ABA content was determined by HPLC-coupled mass spectrometry (HPLC-MS). The results are shown in Table 1. Because of their high ABA content and their palatable taste after an overnight fast (see next paragraph), apricots were chosen for an experiment designed to evaluate whether the intake of ABA-rich food induced an increase of the plasma ABA concentration ([ABA] p).

TABLE 1

ABA content in fruits and vegetables common in the Western diet

| Food | ABA (pmol/g wet weight) | Amount (in g) of food containing approximately 80 µg of ABA |
|---|---|---|
| Fig | 2812.3 | 108 |
| Apricot | 2583.4 | 250 |
| Bilberry | 1444.2 | 200 |
| Banana | 835.4 | 364 |
| Potato | 119.2 | 2542 |
| Soya milk | 117.4 | 2580 |
| Apple (cv. Smith) | 90.2 | 3361 |
| Olive | 62 | 4878 |

The ABA content in various foods was determined by HPLC-MS, as described in the Methods. The amount of food containing approximately 80 micrograms of ABA, i.e. the dose taken by the volunteers in this study, is also indicated.

In order to compare the effect of the plant extracts in rats and in humans apricots were chosen for all experiments because they have a pleasant taste. This vegetal source must be considered illustrative only, without any intention of limitation regarding other possible vegetal matrices for extraction.

The Intake of Apricots Increases the [ABA]p in Healthy Volunteers to a Much Greater Extent Compared to a Glucose Load To explore the bioavailability of ABA contained in food experiments were performed on human volunteers. Due to the high content of endogenous ABA and their pleasant taste we chose apricots for this experiment to assess whether the intake of ABA-rich food induced an increase of [ABA]p.

Four volunteers, fasted for 12 hours, ingested 250 g each of fresh apricots, containing 290 nmol (80 micrograms) of endogenous ABA, determined by HPLC-MS. Blood samples (5 ml) were collected in heparin immediately before (time zero) and 15, 30, 60 and 120 min after the meal, to determine the concentrations of plasma glucose and of [ABA]p. Blood glucose and [ABA]p were compared with the values measured in 12 healthy subjects who underwent an OGTT: 6 were enrolled in this study and 6 were enrolled in a previous one (Bruzzone S. et al., 2012), and their values of glucose and [ABA]p were added to increase the number of controls. The results obtained are shown in FIG. 1.

Figure 1B:
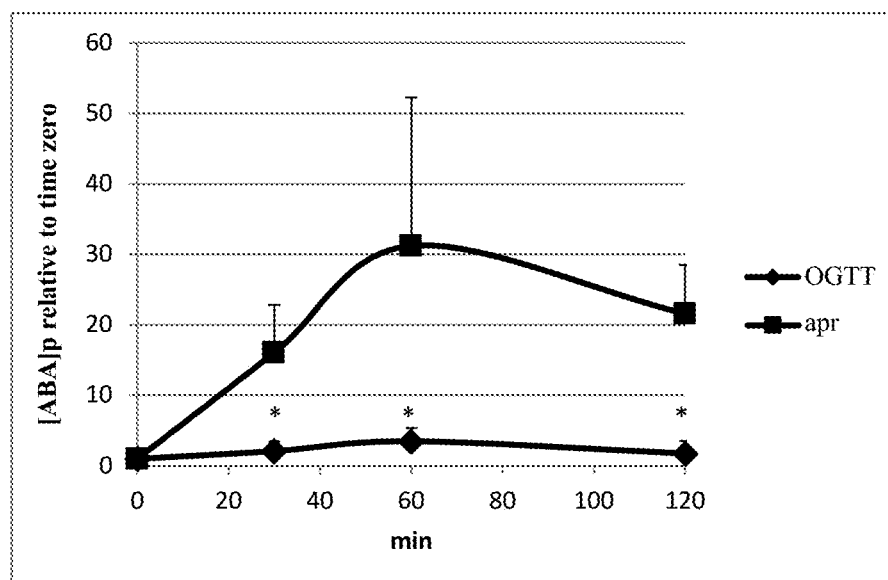
FIG. 1B shows changes in [ABA]p after intake of apricots (apr) or after oral glucose load (OGTT)
Figure 2:
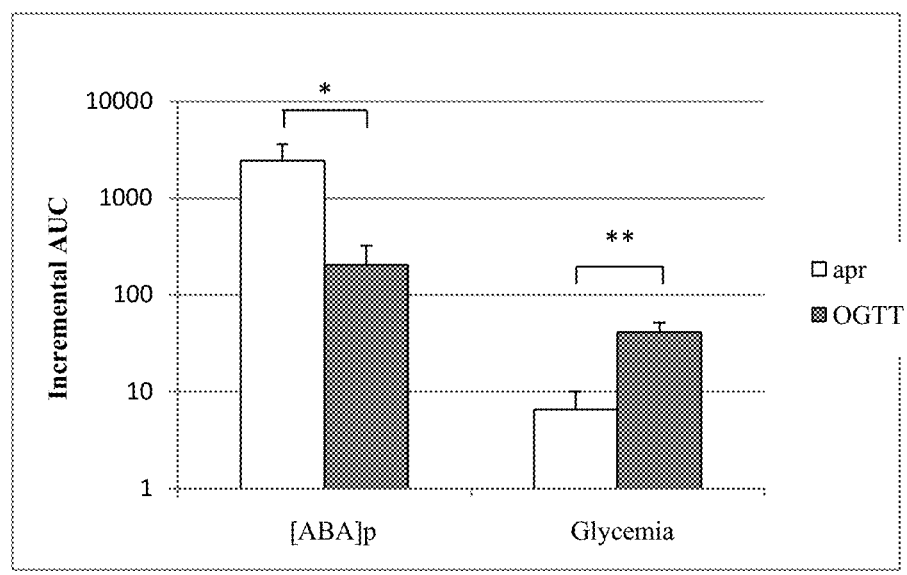
FIG. 2 compared the results shown in FIGS. 1A and 1B.

An oral glucose load is known to induce an increase of [ABA]p (Bruzzone S. et al., 2012). Therefore, an increase of [ABA]p after intake of apricots (containing carbohydrates) was predictable. However, compared to values observed during the OGTT, intake of apricots resulted in a lower increase of blood glucose (FIG. 1A) and, conversely, in a greater increase of the [ABA] p (FIG. 1B). Two of the volunteers who took apricots also subsequently underwent an OGTT without and another with ABA. Therefore, it was possible to compare, in the same subject, the AUC values of glycemia and of [ABA]p after intake of glucose or of apricots. As shown in Table 2, the comparison confirms the lower rise of glycemia and, conversely, the higher increase of the [ABA]p after intake of apricots compared to the glucose load.

It can be concluded that the marked increase of the [ABA]p observed after intake of apricots (23, 10, 42 and 54 times over the baseline in the 4 subjects at 60 min) cannot be attributed to the rise in glycemia. Instead, the high plasma levels of ABA after apricot intake demonstrate a surprisingly high bioavailability of ABA from vegetal source, such as to allow almost complete absorption of the ABA endogenously present in the fruits and its release into the bloodstream. In fact, if all of the ABA present in 250 g of apricots (290 nmoles, as measured by HPLC-MS) were absorbed and distributed throughout the body, the concentration of ABA in the blood could be expected to reach values around 4 nM. In fact, the peak value of the [ABA]p measured in the 4 volunteers (2, 1.7, 22 and 16 nM, respectively) was in this order of magnitude or even higher. The bioavailability of ABA ingested with apricots is therefore close to 100%.

FIG. 1: Intake of apricots (apr), compared to an oral glucose load (OGTT), results in a greater increase of [ABA] p, but a smaller increase of glycemia. After a 12-hour fast, 4 volunteers consumed 250 g of ripe, fresh apricots each. Glycemia and [ABA]p were determined, in duplicate, on blood samples taken before (time zero) and 15, 30, 60 and 120 min after eating. Values obtained were compared with those of 12 healthy subjects who underwent a standard OGTT: 6 subjects were enrolled for this study and 6 others were enrolled in a previous one (Bruzzone S. et al., 2012). The ABA content in apricots or present in traces in the glucose solution used for the OGTT, was 77 and 0.09 µg, respectively, as measured by HPLC-MS.

(A) Glycemia (* p<0.006); (B) [ABA]p (p<0.006); (C) AUC of glycemia and of [ABA]p (* p=0.001; ** p=0.002).

TABLE 2

Comparison between the AUC of [ABA]p and of glycemia after intake of apricots or of glucose (OGTT), in the same subject.

| Subject | AUC | apricots | OGTT |
| --- | --- | --- | --- |
| #1 | [ABA]p | 2147 | 3 |
|  | glycemia | 12 | 36 |
| #2 | [ABA]p | 3076 | 66 |
|  | glycemia | 5 | 15 |

Oral Intake of 1 µg/Kg Synthetic ABA Lowers Glycemia in Rats without Increasing Insulin Levels During an OGTT Overall, results obtained in the experiment with the apricots showed that intake of about 1 µg/Kg BW of ABA increased significantly the [ABA]p in humans. Thus, we investigated whether a similar amount of ABA was sufficient to lower glycemia in rats subjected to an OGTT. It was previously described that intake of ABA improves glucose tolerance in db/db mice, fed a high fat diet (Guri A J et al., 2007), although at an ABA dose of 100 mg/Kg and in mice genetically deficient for the leptin receptor. The dose of synthetic ABA administered to the rats and shown here to be capable of lowering glycemia during the OGTT, was 5 logs (i.e. 100,000 times) lower than the dose previously reported and described as the lowest effective dose able to lower fasting glycemia in mice (100 mg/Kg BW) (Guri A J et al., 2007).

Figure 3A:
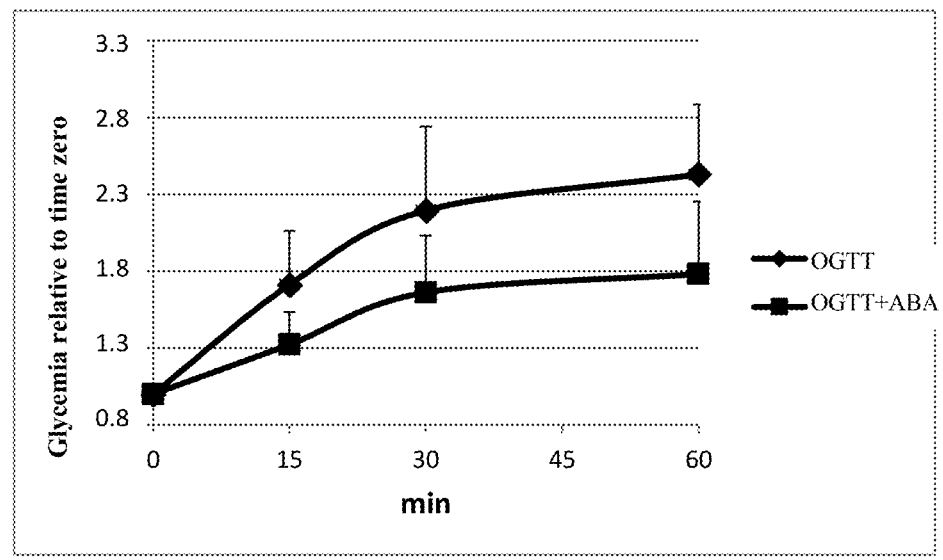
FIG. 3A shows the glycemic profiles of animals treated with ABA.
Figure 3B:
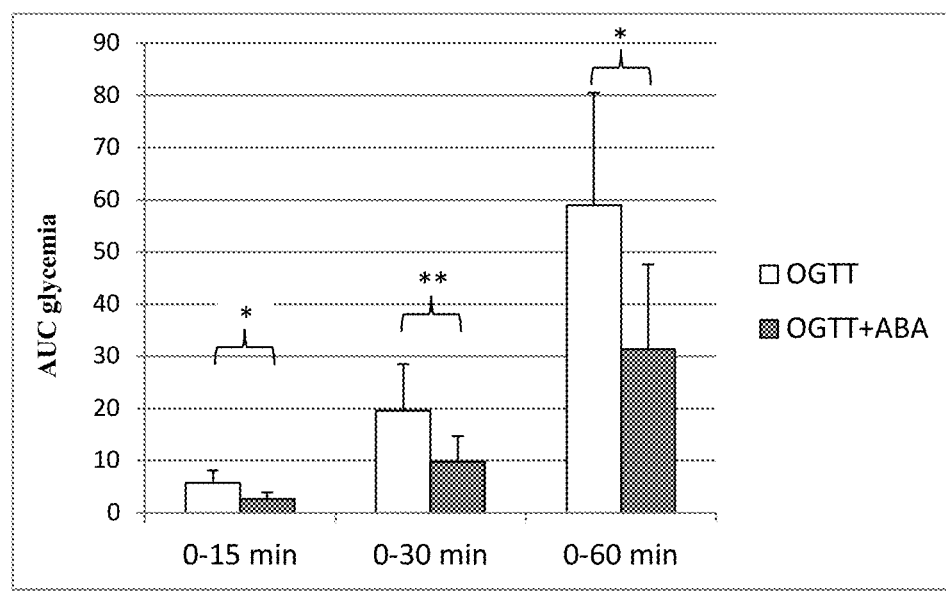
FIG. 3B shows levels of AUC in animals treated with ABA.

Male Wistar rats (12 per group) underwent an OGTT without (controls) or with the addition of 1 µg/Kg BW synthetic ABA to glucose. Results obtained are shown in FIG. 3 and in FIG. 4. Animals treated with ABA showed a significantly reduced glycemic profile compared to the controls (FIG. 3A) and, consequently, a significantly lower AUC of glycemia, which was already reduced in the time frame 0-15 min (FIG. 3B), demonstrating the fast action of orally administered ABA.

Figure 4A:
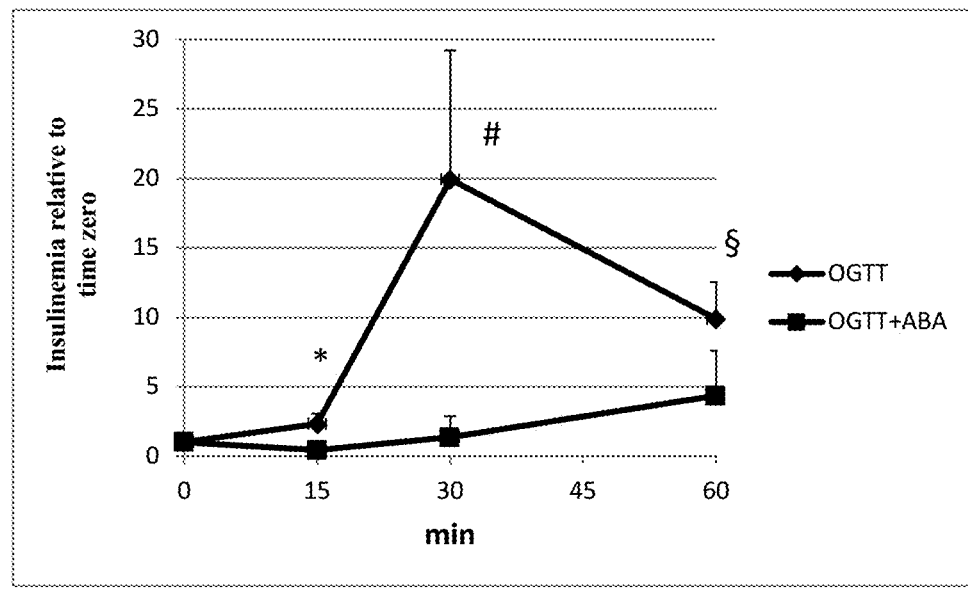
FIG. 4A shows the level of plasmatic insulin in rats subjected to the OGTT in the presence of ABA.
Figure 4B:
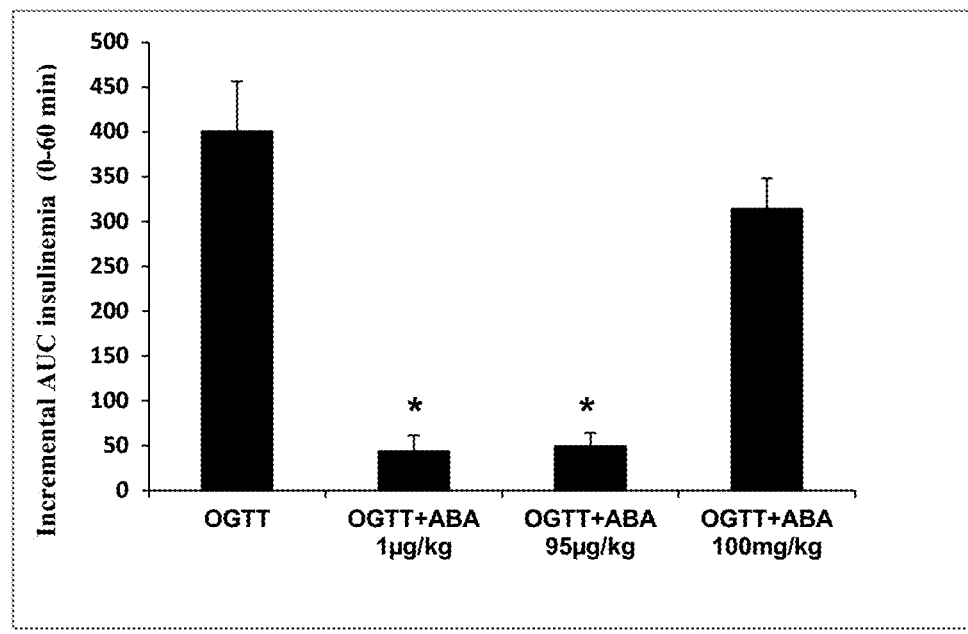
FIG. 4B shows insulin levels in rats treated with ABA.

Surprisingly, the mean level of plasmatic insulin in rats subjected to the OGTT in the presence of ABA was significantly lower compared to controls (FIG. 4A). Consequently, also the insulin AUC in rats treated with ABA was significantly reduced compared to controls (about 15 times, FIG. 4B). For comparison, insulin levels were evaluated during an OGTT in 2 additional groups of rats (12 per group) treated with ABA at 95 µg/Kg BW or 100 mg/Kg BW. These two doses represent the maximum dose used by the inventors in this study and the dose previously described (Guri A J et al., 2007) as the lowest effective dose capable of reducing glycemia in mice, respectively. Also at these doses, the glycemic profile of the ABA-treated animals was reduced compared to the controls, but at the dose of 100 mg/Kg BW the insulin AUC was comparable to that of control rats and significantly higher than that of rats treated with 1 or 95 µg/Kg BW ABA (FIG. 4B). Therefore, unexpectedly, the in vivo mechanism underlying the glucose lowering effect of ABA at 1 µg/Kg BW is not dependent on stimulation of insulin release, as would have been predictable from the in vitro results, where ABA stimulated insulin release from both human pancreatic beta cells and from rat insulinoma cells (Bruzzone S. et al., 2008), and as occurs at the dose of 100 mg/Kg BW, previously described as the lowest effective dose having hypoglycemic effect in vivo (Guri A J et al., 2007).

Therefore, in contrast with the previous literature, the inventors demonstrate not only that a dose of ABA 5 logs lower than that reported in the literature induces hypoglycemic effects in vivo, but also that the intake of ABA at the dose of 1 and up to 95 µg/Kg BW generates a significant decrease in the insulin response to the glucose load (FIG. 4B). This result was not inferable from previous studies (Guri A J et al., 2010), where insulin levels was not even measured after glucose load, but rather after fasting, and were not significantly lower in ABA-treated animals compared to controls. It is known that the fasting insulin level is not predictive of the insulinemic response to an increased glycemia during glucose load: if it were, a single dosage of fasting insulin levels would suffice for diagnosis of diabetes mellitus. Instead, the diagnostic criteria for diabetes mellitus are different (ADA/EASD Diabetes diagnosis & management guidelines 2015). Moreover, the inventors demonstrate that, at a dose of 100 mg/Kg BW (as in Guri A. J. et al., 2007 and 2010), ABA induces an insulin response which is not significantly lower than that of control (FIG. 4B). Therefore, the inventors demonstrate that the underlying mechanism of glycemic control operated on by ABA is different at the dose of 1 µg/Kg compared to the dose of 100 mg/Kg BW already reported in the literature: at 100 mg/Kg, the glucose lowering effect of ABA is due to insulin release by the pancreas, while at a dose of 1 µg/Kg, the glucose lowering effect of ABA is independent from insulin secretion, which conversely is saved. This experimental result rules out that ABA at a dose of 1 µg/Kg (corresponding to a plasma concentration of less than 10 nM) could have determined an activation of the transcription factor PPAR-gamma, for which a minimum concentration of 100 mg/Kg BW ABA is required, as expressly reported by the authors (Bassaganya-Riera J et al, US2007/0184060 A1). Therefore, the results obtained by the inventors were not inferable from the previous literature, which established the following sequence of events, triggered by the reportedly minimal effective dose of ABA of 100 mg/Kg: PKA activation→activation of PPAR-gamma→increased insulin release from beta-pancreatic cells→lowering effect on glycemia (Bassaganya-Riera et al. 2011, J Obesity doi: 10.1155/2011/897894).

FIG. 3 and FIG. 4: Oral intake of synthetic ABA at a dose of 1 µg/Kg BW lowers glycemia in rats without increasing insulin levels during an OGTT. Two groups of male Wistar rats (12 animals per group), fasted for 17 hours, were subjected to an OGTT (1 g/Kg BW glucose), without or with 1 µg/Kg BW of synthetic ABA. Glycemia was measured with a glucometer in duplicate on blood taken from the tail vein at baseline (immediately before gavage) and at the indicated times after gavage. Insulinemia was measured by ELISA, in duplicate on plasma samples. Results are mean±SD.

(A) glycemia relative to time zero, * p=0.002; #p=0.008; § p=0.002 OGTT+ABA vs. OGTT; (B) AUC glycemia, * p=0.001; ** p=0.002 OGTT+ABA vs. OGTT; (C) insulinemia relative to baseline * p=0.002; #p=0.01; § p=0.02 OGTT+ABA vs. OGTT; (D) incremental AUC of insulinemia during OGTT without or with ABA at the doses of 1 µg/Kg BW, 95 µg/Kg BW or 100 mg/Kg BW, * p=0.009 AUC OGTT vs. OGTT+ABA at 1 µg/Kg and 95 µg/Kg.

Figure 5A:
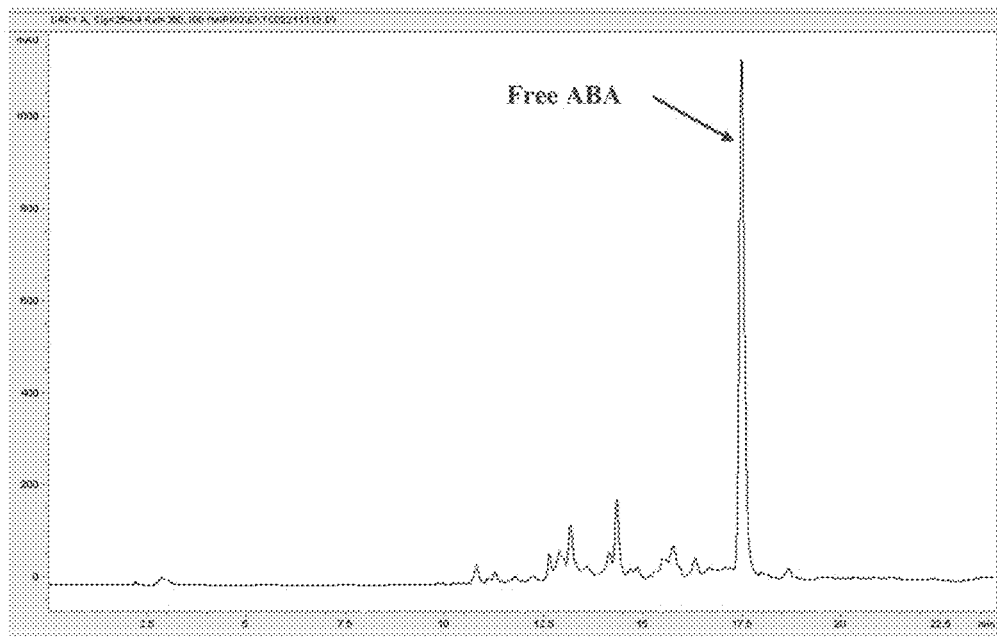
FIGS. 5A and 5B show HPLC-MS analysis of an aqueous apricot extract.
Figure 5B:
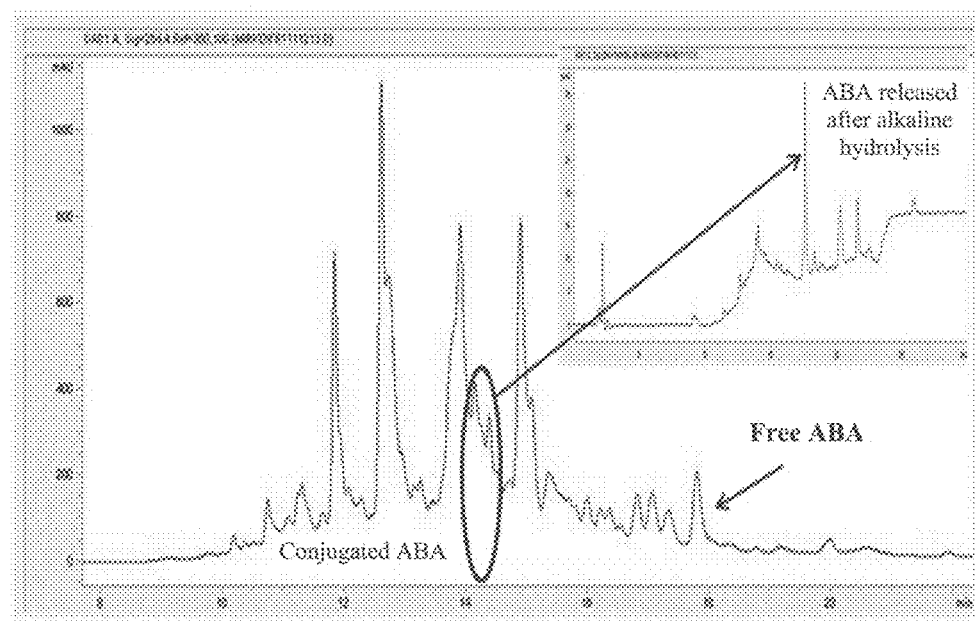

Supercritical $CO_2$ and Aqueous Apricot Extracts Contain ABA or ABA and ABA-GE, Respectively To confirm the efficacy of the dose of synthetic ABA tested in the OGTT on rats with ABA naturally present in vegetals, a supercritical $CO_2$ or an aqueous apricot extract were prepared, containing an amount of ABA similar to the one previously administered as a synthetic compound. The HPLC-MS analysis confirmed the presence of ABA (without ABA-GE) in the supercritical $CO_2$ extract (FIG. 5A) and of ABA together with ABA-GE in the aqueous extract (FIG. 5B), at a concentration of 5.6±1.8 and 14.3±2.9 micrograms per gram of extracted apricots, for ABA and ABA+ABA-GE, respectively (n=8). On the basis of these values, the dose of extract was calculated to yield a total amount of ABA and of ABA+ABA-GE administered to each rat during the OGTT (FIG. 6) of 1.1 and 0.9 µg/Kg BW, respectively.

FIG. 5: HPLC-MS analysis of supercritical $CO_2$ and aqueous apricot extracts. The amount of non-conjugated ABA (free ABA) contained in the supercritical $CO_2$ extract (A) and in the aqueous extract (B) were measured by HPLC-MS. The fraction of the aqueous extract eluted from the column between 14 and 14.5 minutes was collected, subjected to alkaline hydrolysis to hydrolyze the ABA glucoside ester and further analyzed by HPLC-MS to determine the amount of free ABA derived from its conjugated form (inset).

ABA-GE Taken Orally is Hydrolyzed to ABA In Vivo.

Figure 6:
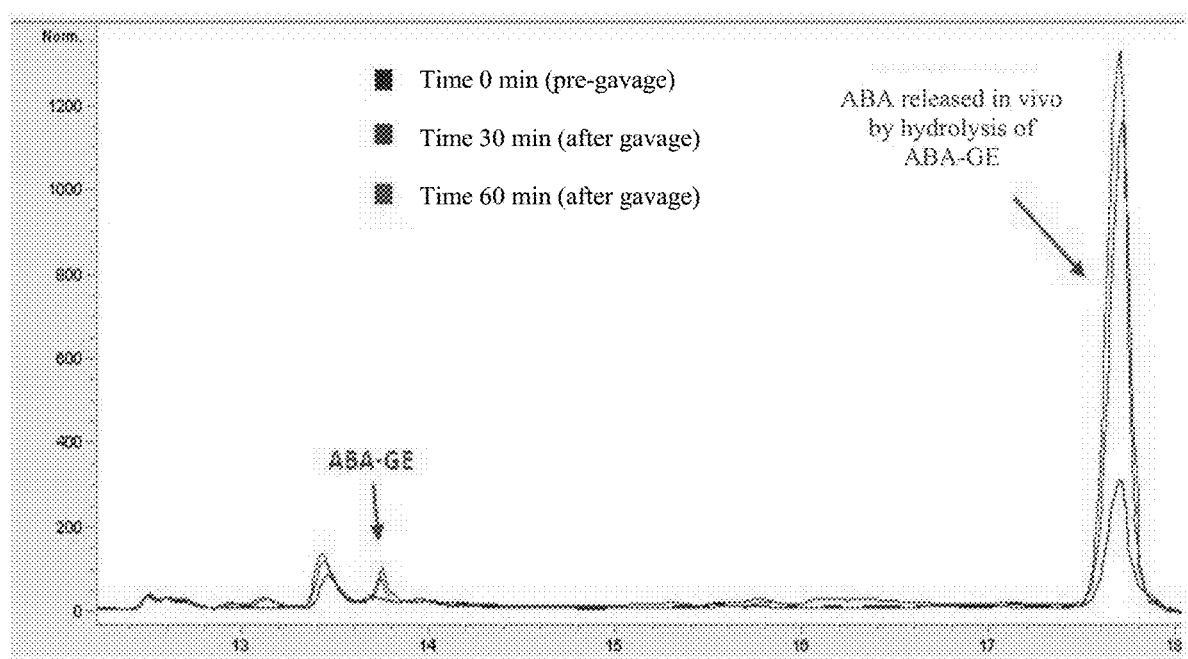
FIG. 6 shows HPLC-MS analysis of representative plasma sample from a rat subjected to gavage with a solution containing synthetic ABA-GE.

Wistar rats (n=3) were given an amount of synthetic ABA-GE by gavage in order to evaluate its in vivo hydrolysis, resulting in the release of ABA. The chromatographic analyses performed on plasma samples at 30 and 60 min after gavage, compared to the values of [ABA]p at 0 min, immediately before gavage, show a marked increase of the chromatographic peak of free ABA (FIG. 6). This result indicates that the oral intake of ABA-GE is followed by its in vivo hydrolysis, resulting in the appearance of free ABA in the bloodstream. Therefore, the ABA-GE present in the aqueous apricot extract contributes to the effective dose of ABA taken with the extract, as it can be hydrolyzed to yield free ABA.

FIG. 6: HPLC-MS analysis of representative plasma samples from a rat subjected to gavage with a solution containing synthetic ABA-GE. The figure shows the overlapping of 3 chromatograms relative to time 0 (pre-gavage), 30 and 60 min (post-gavage), obtained from the methanol extraction and HPLC analysis of three different plasma samples. The amount of ABA released by hydrolysis from its conjugated form ABA-GE at different times (30 and 60 min after gavage) was measured by HPLC-MS. The coefficient of absorbance of ABA-GE at 254 nm, used for chromatographic analysis, is approximately 10 times lower than that of free ABA. This explains the different area of their respective chromatographic peaks.

Figure 7:
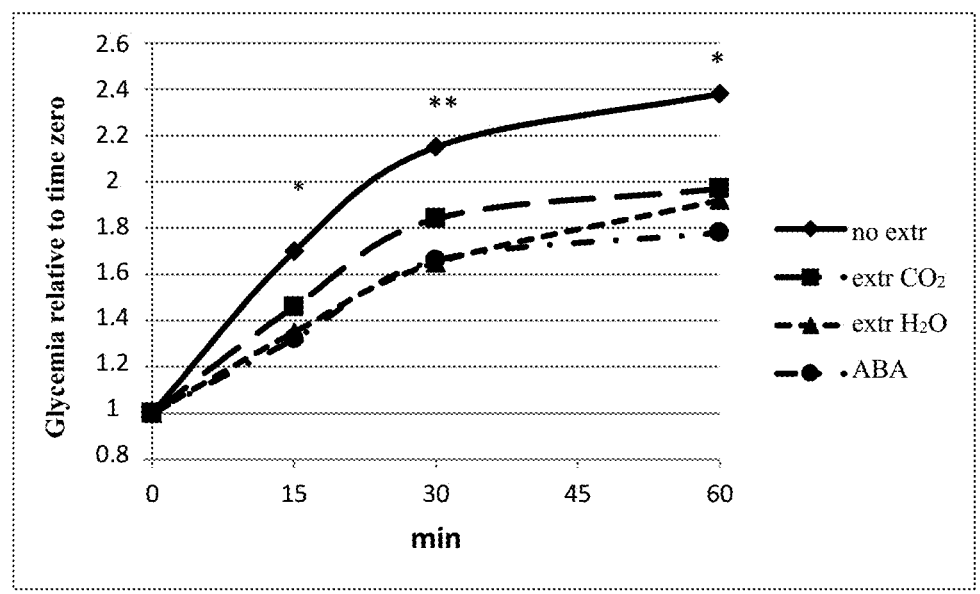
FIG. 7 shows that supercritical $CO_2$ or aqueous apricot extracts improve tolerance in rats.

Supercritical $CO_2$ or Aqueous Apricot Extracts Improve Glucose Tolerance in Rats Wistar rats (10 per group) were subjected to an OGTT without (control) or with the addition of the extracts to the glucose solution. The supercritical $CO_2$ extract significantly reduced the blood glucose level in the treated animals compared to the controls (FIG. 7). In the case of the aqueous extract, it is likely that an unknown amount of carbohydrates contained in the extract was also administered to the treated animals, and therefore the glucose lowering effect of the extract could be underestimated. Nonetheless, the glycemic profile in animals treated with the aqueous extract was significantly reduced compared to the controls, similarly to what observed with the supercritical $CO_2$ extract (FIG. 7), which certainly does not contain carbohydrates as they are insoluble in the supercritical $CO_2$. The comparison between the efficacy of the same dose of ABA given to the rats as a synthetic molecule or endogenously present in the extracts, shows that the glycemic profile of the animals treated with ABA present in the extracts is not significantly different from that of animals treated with synthetic ABA (FIG. 7).

FIG. 7: Supercritical $CO_2$ or aqueous apricot extracts improve glucose tolerance in rats. Male Wistar rats, aged 9-13 weeks, were divided into 3 groups (10 animals per group) and fasted for 17 hours. After mild sedation with diazepam, 1 g/Kg BW of glucose in 300-400 µl water was administered by gavage to each animal, without (no extr) or with a supercritical $CO_2$ (extr $CO_2$) or aqueous (extr $H_2O$) apricot extract. Immediately after gavage, rats were anesthetized with xylazine and ketamine. Glycemia was measured on blood taken from the tail vein with a glucometer immediately before gavage (time zero) and 15, 30 and 60 min after gavage. Each measurement was performed in duplicate. (*) $p<0.05$ (**) $p<0.005$ no extr compared with all other curves.

Intake of a Supercritical $CO_2$ Apricot Extract Lowers Glycemia During OGTT in Three Healthy Volunteers We explored whether the intake of a supercritical $CO_2$ apricot extract, containing the same dose of endogenous ABA as that introduced by each volunteer with 250 g of fresh apricots (FIG. 1) or administered with the OGTT to rats (FIG. 7), could lower glycemia during a standard OGTT in humans. Two of the subjects who participated in the experiment with apricots also participated in this experiment. In addition to the 6 OGTT already performed in a previous study (Bruzzone S. et al., 2012), 6 new healthy adult volunteers were recruited for as many OGTT, to increase the number of controls.

Figure 8A:
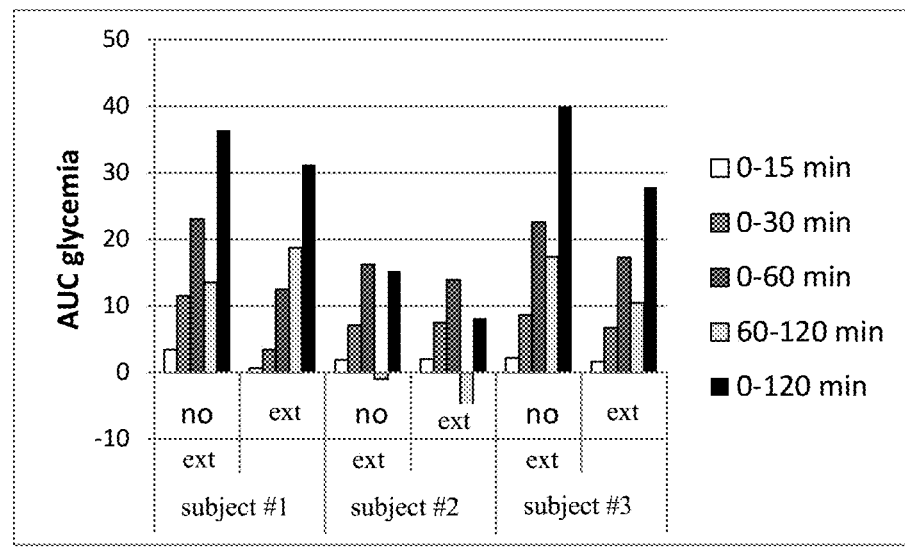
FIG. 8A shows AUC of glycemia in three subjects.
Figure 8B:
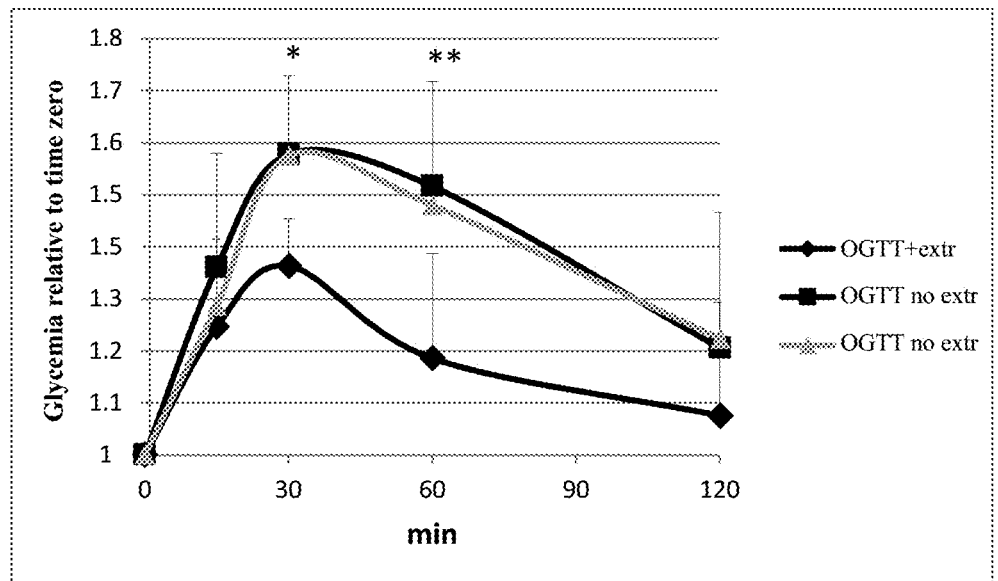
FIG. 8B shows the comparison between the glycemic curves of subjects treated or untreated with the extract.
Figure 9A:
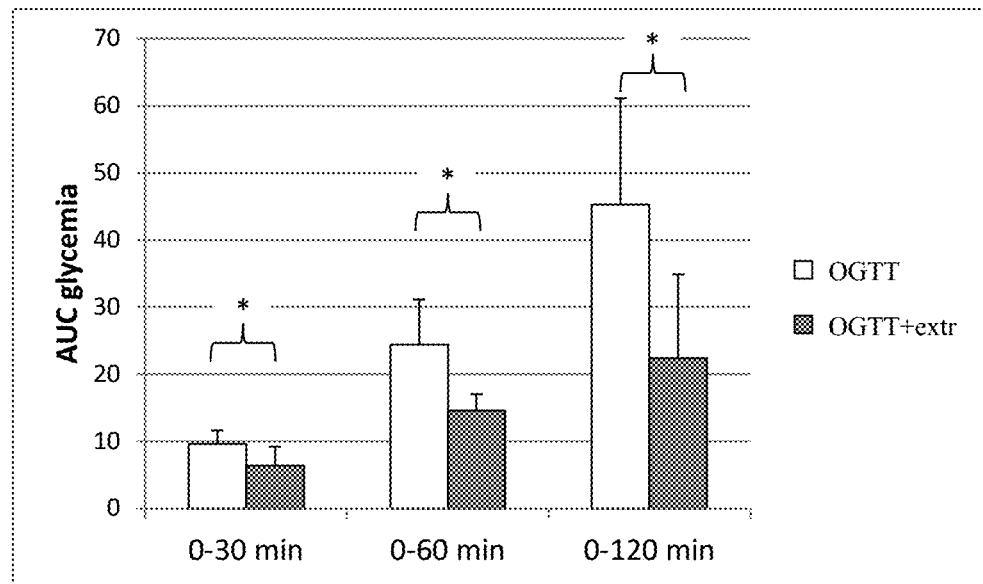
FIG. 9A shows the AUC glycemia in three subjects.
Figure 9B:
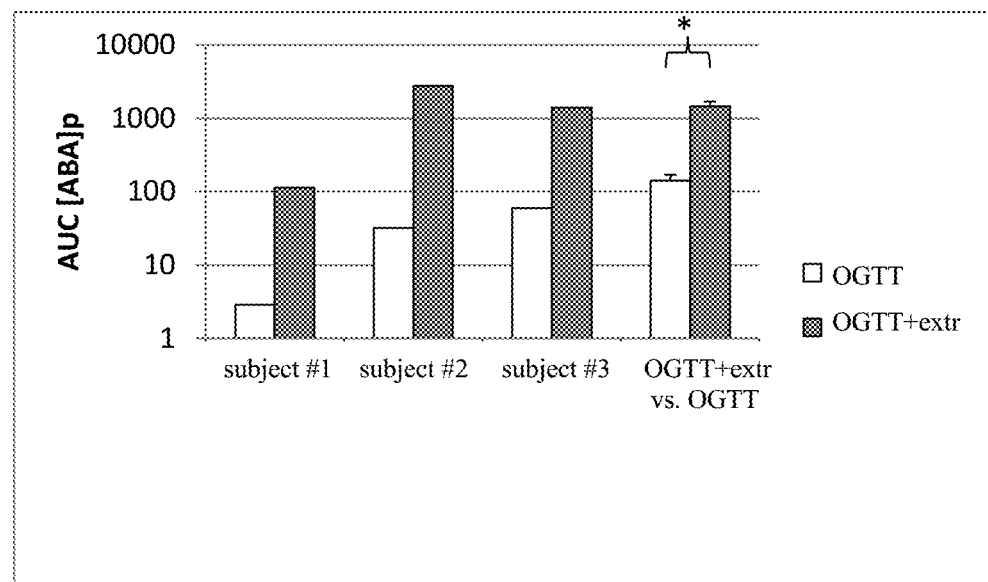
FIG. 9B shows the AUC [ABA]p in three subjects.
Figure 10:
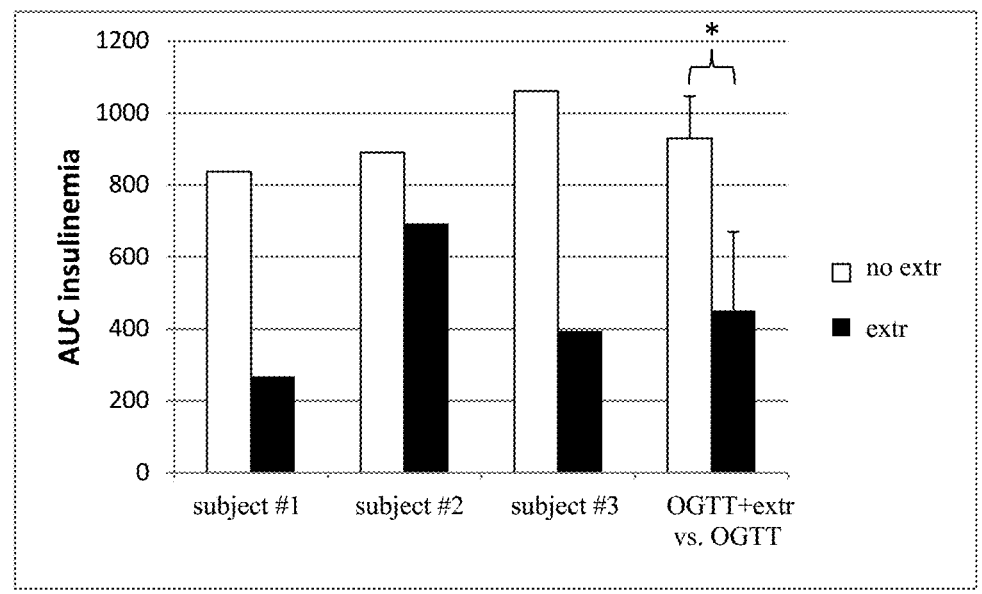
FIG. 10 shows the AUC insulinemia in three subjects.

The results obtained are shown in FIG. 8 and FIG. 9. In all three subjects who underwent the OGTT with the extract, the AUC of glycemia calculated over the entire time-frame (0-120 min) was lower compared with the OGTT without extract (values with or without extract were 31.2 vs. 36.4, 8.1 vs. 15.2, 27.8 vs. 40.1 in subjects #1, #2 and #3, respectively, see FIG. 8A). Subject #1 responded rapidly to the extract, because the major difference between the AUC of glycemia with or without extract was observed between 0 and 30 min (3.4 vs. 11.5) and between 0 and 60 min (12.5 vs. 23.0). Conversely, subjects #2 and #3 had a delayed response to the extract, because the biggest difference between the AUC of glycemia in the presence or absence of the extract was observed between 0 and 60 min (13.9 vs. 16.2 and 17.3 vs. 22.6 in subjects #2 and #3, respectively) and between 60 and 120 min (−6 vs. −1 and 10.5 vs. 17.4 in subjects #2 and #3, respectively).

FIG. 8 and FIG. 9: Intake of a supercritical $CO_2$ apricot extract reduces glycemia during an OGTT in three volunteers. Three healthy subjects underwent two different OGTT, 1 week apart, one without and one with an extract, yielding a dose of ABA of 1.24, 1.24 and 0.83 µg/Kg BW in subjects #1, #2 and #3, respectively (see Materials and Methods for details). Blood samples were taken in heparin 15 min before intake of glucose (time zero) and after 30, 60 and 120 min. [ABA]p and glucose concentrations were measured as described under Materials and Methods. (8A) AUC of glycemia in the three subjects during the indicated time frames after glucose intake; (8B) Comparison between the glycemic curves between the subjects treated with (n=3) or without (n=12) extract. The latter group comprises the same subjects as in FIG. 1A. The grey trace indicates the mean glycemia values measured in 6 volunteers from a previous study, during an OGTT without extract (Bruzzone S. et al., 2012). * $p=0.037$ and ** $p=0.03$ for OGTT vs. OGTT+extr; OGTT no extr n=12; OGTT+extr n=3; OGTT no extr n=6. (C) AUC of glycemia (* $p<0.05$ OGTT vs. OGTT+extr). (9A) AUC of ABAp (* $p=0.031$ OGTT vs. OGTT+extr) and of insulinemia (9B) (* $p=0.03$ OGTT vs. OGTT+extr) in the three subjects during the OGTT without and with extract, in the time frame 0-120 min. Mean values of the AUC during the OGTT with extract (n=3) were also compared (9A and 9B) with the corresponding mean values measured during standard OGTTs without extract (n=12). The latter group comprises the same subjects as in FIG. 1A. * $p<0.05$.

TABLE 3

AUC values of glycemia, [ABA]p and insulinemia during OGTT with the supercritical $CO_2$ extract, compared with the corresponding values measured during an OGTT without extract, in three volunteers.

|  | Subject #1 (1.24 µg ABA/Kg BW) | | | Subject #2 (1.24 µg ABA/Kg BW) | | | Subject #3 (0.83 µg ABA/Kg BW) | | |
| --- | --- | --- | --- | --- | --- | --- | --- | --- | --- |
|  | glyc | [ABA]p | ins | glyc | [ABA]p | ins | glyc | [ABA]p | ins |
| min 0-30 | 0.29 | 2.6 | 0.18 | 1.20 | 6.5 | 0.96 | 0.77 | 20 | 0.39 |
| min 0-60 | 0.54 | 4.0 | 0.22 | 0.85 | 2.4 | 0.88 | 0.77 | 32 | 0.42 |
| min 0-120 | 0.85 | 39.7 | 0.32 | 0.53 | 1.8 | 0.77 | 0.69 | 129 | 0.42 |

Three subjects underwent two different OGTT each, one without and one with a supercritical $CO_2$ apricot extract (containing the indicated dose per Kg BW), taken with the glucose. Glycemia, [ABA]p and insulinemia were measured at time zero (immediately before glucose intake) and after 15, 30, 60 and 120 min (see Materials and Methods for details). The incremental AUC of the plasma concentrations of glucose (glyc), ABA ([ABA]p) and insulin (ins) were calculated over the indicated time frames. Results are expressed as AUC in the OGTT with extract relative to the corresponding AUC in the OGTT without extract, in each subject.

Intake of an Aqueous Apricot Extract Reduces Glycemia During an Experimental Lunch in Three Volunteers To investigate the effect of an aqueous apricot extract on a carbohydrate intake more physiological than the OGTT, three volunteers consumed the same breakfast and lunch (B&L), either without (B&L no extr) or with (B&L+extr) an aqueous apricot extract containing a dose of ABA (comprising ABA and ABA-GE, henceforth defined as "total ABA") of approximately 1 μg/Kg, taken immediately before breakfast. The composition of the standard meals is shown in Table 4, together with the content in endogenous ABA of the food (approx. 7 μg).

Figure 11A:
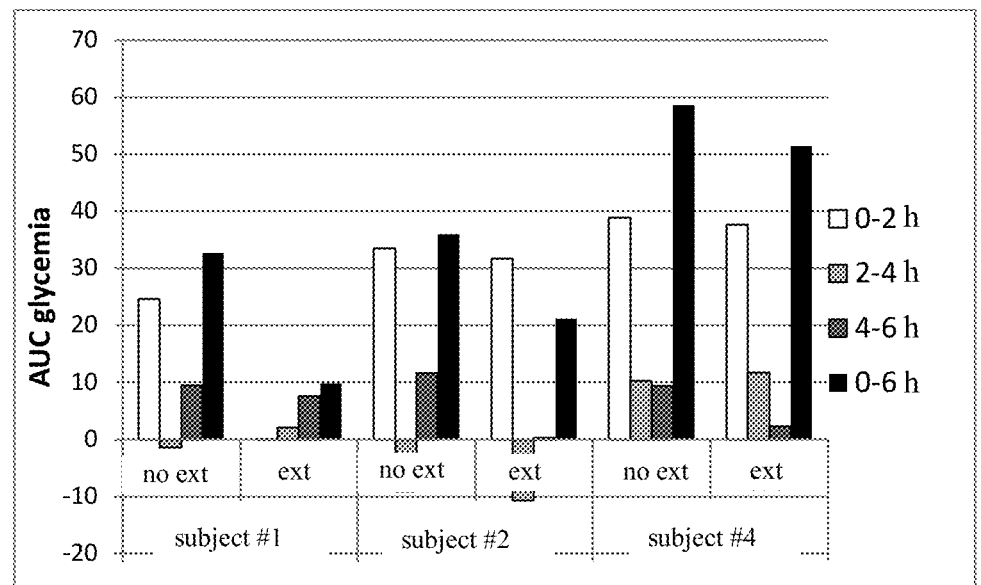
FIG. 11A shows the AUC glycemia in three subjects
Figure 11B:
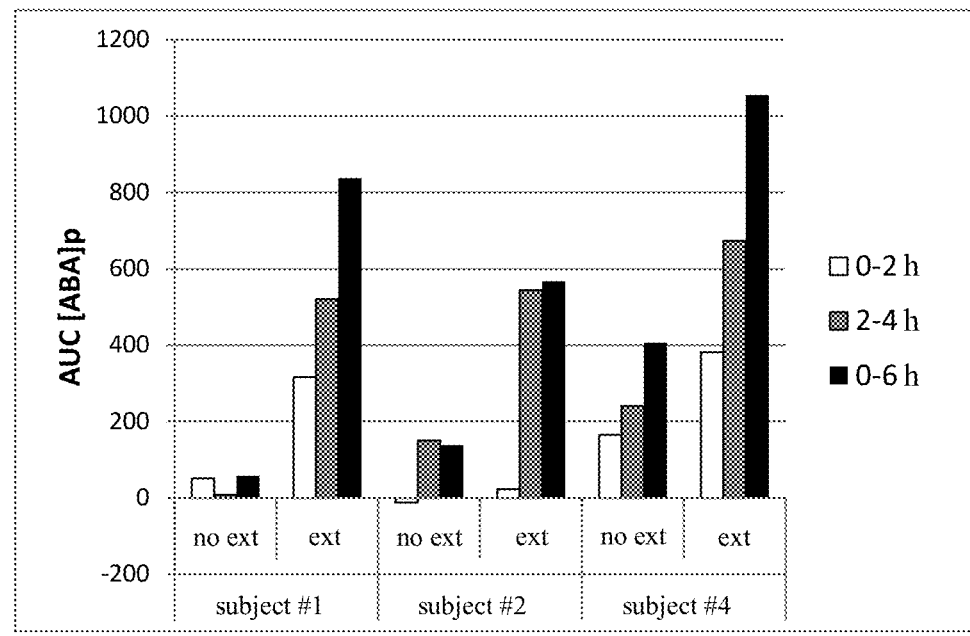
FIG. 11B shows the AUC [ABA]p in three subjects.
Figure 12A:
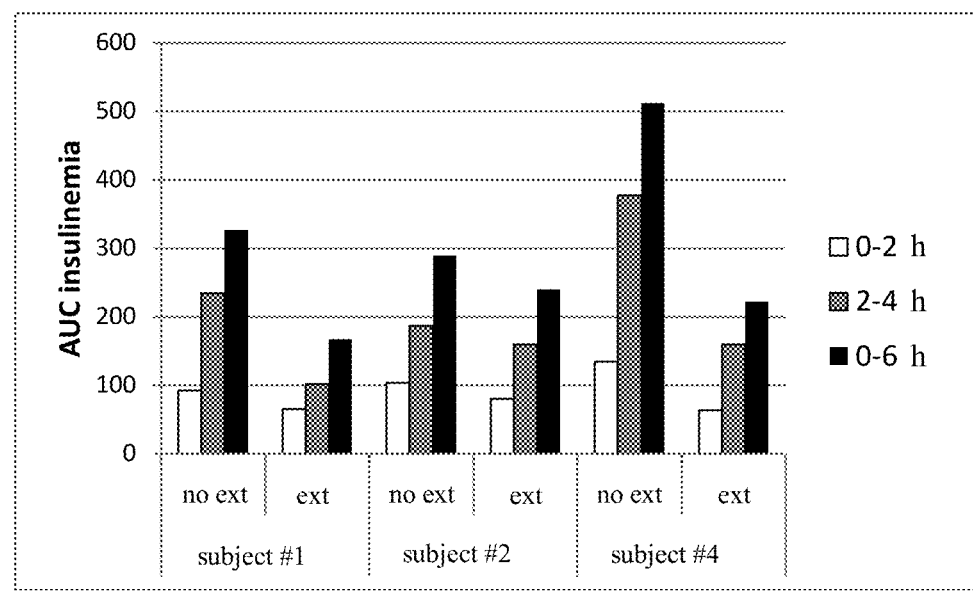
FIG. 12A shows the AUC insulinemia in three subjects.
Figure 12B:
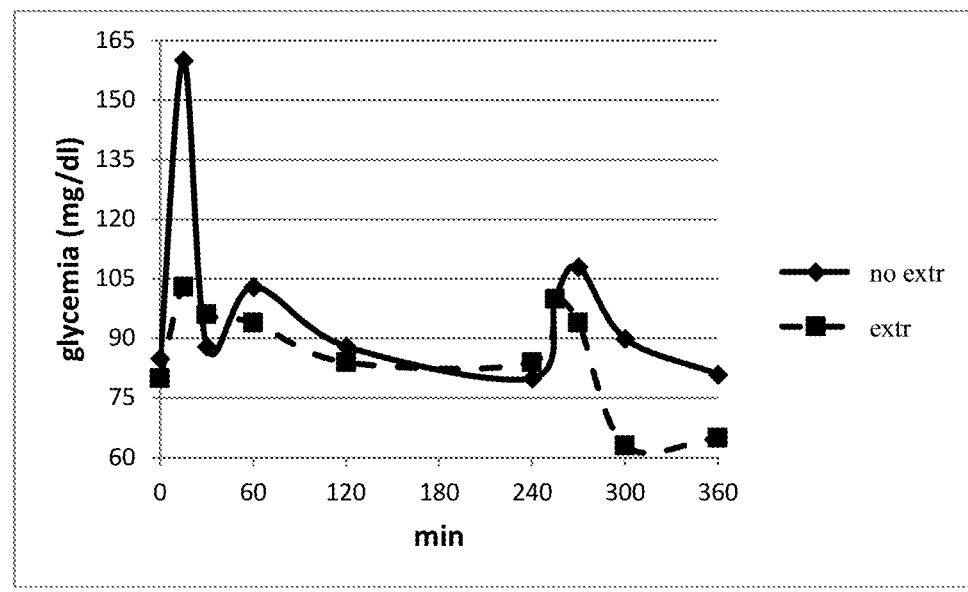
FIG. 12B shows a representative glycemic profile of a subject.

Thus, the total dose of ABA in the B&L+extr was approx. 1 log higher compared to that in the B&L no extr. Glycemia, insulinemia and [ABA]p were measured on blood samples taken immediately before breakfast (time zero), 2 and 4 hours after breakfast (the latter time point being immediately before lunch) and 2 hours after lunch. Results obtained are shown in FIG. 11 and FIG. 12. In all subjects, a reduction of the AUC of glycemia was observed in the time frame 0-6 hours in the meal with extract compared to the meal without extract (FIG. 11A).

Subject #1 was again an "early responder": as already observed in the OGTT, the major difference between the AUC of glycemia in the presence or in the absence of extract was observed after breakfast, in the time frame 0-2 hours (the corresponding values were 0.1 vs. 24). However, the hypoglycemic action of the extract was evident also after lunch, in the time frame 4-6 hours (AUC values of glycemia were 7.6 and 9.5 with and without extract, respectively). Conversely, subjects #2 and #4 were "late-responders", as the major difference between the AUC of glycemia in the presence or in the absence of the extract were observed after lunch, in the time frame 4-6 hours (the corresponding values were 0.25 vs. 11.6 and 2.3 vs. 9.4 in the two subjects, with or without extract, respectively).

Thus, in all subjects, intake of the extract before breakfast reduced the AUC of glycemia after lunch (Table 5): notwithstanding the individual variability, the difference between the mean AUC of glycemia measured in the experiments B&L+extr compared to the experiments B&Lno extr was statistically significant (p=0.04). This fact indicates that the hypoglycemic action of the extracts lasts for at least 6 hours after administration. Indeed, in all subjects, the AUC of [ABA]p was significantly higher in the B&L+extr experiment compared with the B&Lno extr (FIG. 11B).

The values of the AUC of insulinemia as calculated in the time frame 0-6 hours were conversely lower in the experiment with the extract compared with the experiment without extract, in all subjects (FIG. 12A): the values of the AUC of insulinemia after intake of the extract were 0.5, 0.8 and 0.4 relative to those measured in the experiment without extract, in subjects #1, #2 and #4, respectively. Absorption of ABA was apparently slower in subject #2 compared with the other volunteers, because the AUC of [ABA]p showed only a slight increase in the time frame 0-2 hours (FIG. 12A): it is noticeable that at the same time points, the AUC of glycemia and insulinemia were similar to those in the experiment without extract, in line with the apparent reduced effect of the extract in the time frame 0-2 hours in this subject.

FIG. 11 and FIG. 12 Intake of an aqueous apricot extract reduces glycemia during a carbohydrate-rich meal.

After 12 hours fasting, three volunteers consumed a standard breakfast and, 4 hours later, a standard lunch (see Table 4 for the composition), without (no extr) or with 77 μg ABA contained in an aqueous apricot extract (extr), taken immediately before breakfast. The two experiments were performed 1 week apart (see Materials and Methods for details). Immediately before breakfast (time zero) and 2 hours, 4 hours (immediately before lunch) and 6 hours after breakfast capillary glycemia was measured with a glucometer and blood samples were taken in heparin for determination of [ABA]p and of insulinemia. Each value was determined in duplicate, with similar results. For each subject, the values of the AUC of glycemia (11A), of [ABA]p (11B) and of insulinemia (12A) are shown as calculated over the indicated time frames in the experiment without (no extr) or with extract (extr). (12B) A representative glycemic profile of a subject is shown.

TABLE 4

Composition of the standard meals.

| Meal | Fodd | Endogenous ABA content |
|---|---|---|
| Breakfast | Cookies (Oro Saiwa) (96 g) Whole milk (175 ml) Apricot jam (40 g) | 6.4 μg |
| Lunch | Spaghetti (180 g) Olive oil (5 g) Yogurth (125 g) | 0.97 μg |

TABLE 5

AUC of glycemia during the standard meal with the aqueous apricot extract relative to that during the meal without extract.

| | Subject #1 | Subject #2 | Subject #4 |
|---|---|---|---|
| | Total dose of ABA (μg/Kg BW) | | |
| B&L + extr | 1.36 | 1.21 | 1.58 |
| B&L no extr | 0.11 | 0.10 | 0.13 |
| | AUC of glycemia B&L + extr/B&L no extr | | |
| 0-2 hours | 0.004 | 0.92 | 0.98 |
| 4-6 hours | 0.27 | 0.02 | 0.07 |
| 0-6 hours | 0.11 | 0.71 | 0.64 |

After 12 hours fasting, three volunteers ate the same breakfast and, 4 hours later, the same lunch (see Table 4 for the composition). Capillary glycemia was measured in duplicate before breakfast (time zero) and after 2, 4 and 6 hours. After 1 week, the same subjects ate the same breakfast and lunch, but taking the aqueous extract before breakfast. Results are expressed as AUC of glycemia during the breakfast and lunch with extract (B&L+extr) relative to the AUC during the breakfast and lunch without extract (B&L no extr). The total amount of ABA present in the extract taken by each subject is indicated in the Materials and Methods. ABA endogenously present in the food was <10% of the amount present in the extract.

Oral Daily Intake of Synthetic ABA at the Dose of 1 μg/Kg Reduces the Increase of Body Weight Induced by Chronic High-Dose (1 g/Kg) Glucose Intake in the Mouse We wanted to verify whether the saving of insulin observed in the acute glucose load experiments with ABA could induce a diminished insulin-induced synthesis and deposition of triglycerides, and consequently a diminished weight increase, during chronic treatment with the same concentrations of glucose and ABA. Female CD1 mice (outbred) (9 per group) were administered daily a glucose solution, without (controls) or with synthetic ABA, with the drinking water. The amount of glucose and of ABA dissolved in the water were calculated taking into consideration the daily volume of drinking water consumed by each animal so as to reach a dose of 1 g/Kg BW and 1 μg/Kg BW for glucose and for ABA, respectively. After 12 weeks, the animals treated with ABA together with the glucose showed a significantly lower weight increase compared to the controls (FIG. 13), in line with the reduced insulin secretion observed in the OGTT experiments (FIG. 4A, B). Indeed, insulin is known to stimulate the synthesis and accumulation of triglycerides in the adipose tissue, which cause the increase of body weight observed following a carbohydrate-rich diet.

The reduced body weight increase in the mice chronically treated with ABA at 1 µg/Kg compared to the controls (FIG. 13) contrasts sharply with the weight increase, not dissimilar compared with the controls, reported in the literature in mice chronically treated with ABA at 100 mg/Kg BW (Guri A. J. et al., 2007; Bassaganya-RieraJ. et al., US2007/0184060 A1, 2007). The reduction of body weight increase in the animals chronically treated with ABA at 1 µg/Kg compared to the controls reported by the inventors is a further confirmation of the different mechanism of action of ABA at the dose of 1 µg/Kg compared with the dose of 100 mg/Kg reported in the literature; the similar weight increase in the animals treated with ABA at 100 mg/Kg and in the controls is indeed in agreement with the absence of reduction of insulin release in the treated animals compared with the controls (FIG. 4B).

Figure 13:
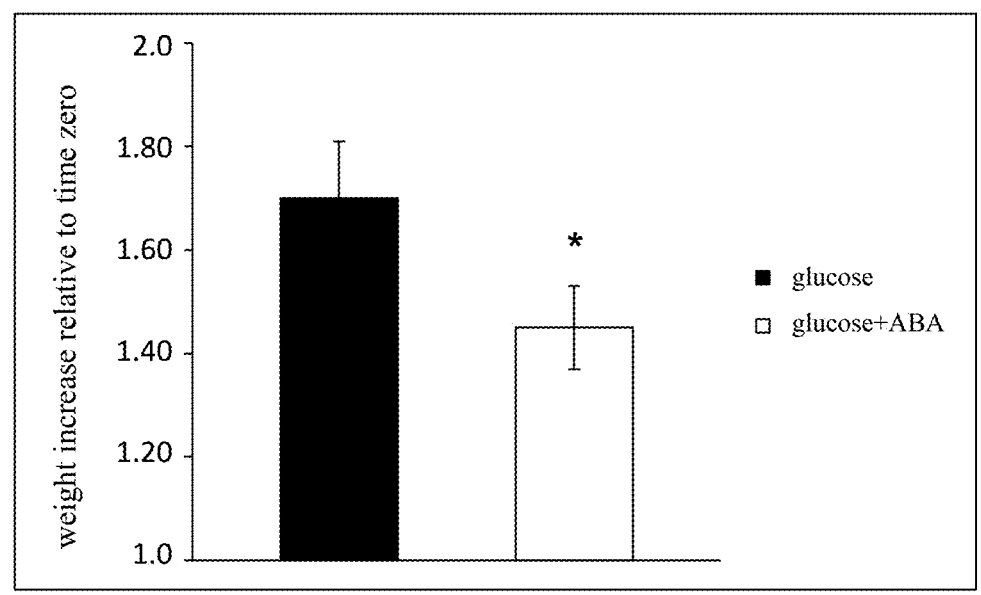
FIG. 13 shows the weight increase relative to time zero in animals treated with glucose with or without ABA.

FIG. 13. Daily oral intake of synthetic ABA at the dose of 1 µg/Kg reduces the body weight increase induced by the chronic intake of high-dose glucose (1 g/Kg) in mice. Five-week old female CD1 mice (outbred) (9/group) received daily, in the drinking water, a glucose solution without (controls) or with synthetic ABA (see Materials and Methods for details). Body weight was determined after 12 weeks of treatment, and both groups of animals were fasted for 17 hours before measurement. The reason for choosing female animals for this experiment rests in their natural predisposition to accumulate fat, which is not observed in the males from the same strain.

* $p<0.01$ glucose vs. glucose+ABA.

Daily Oral Intake of Synthetic ABA at the Dose of 1 µg/Kg Improves Muscle Performance in Mice Male CD1 mice (outbred) (8/group) were administered daily a glucose solution with the drinking water, without (controls) or with the addition of synthetic ABA. The amount of glucose and of ABA dissolved in the water were calculated taking into consideration the daily volume of drinking water consumed by each animal so as to reach a dose of 1 g/Kg BW of glucose and 1 µg/Kg BW of ABA. After 12 weeks, a wheel with a digital cyclometer was placed in each cage. The animals treated with ABA together with the glucose showed a significant improvement of the muscular endurance. Mice treated with glucose+ABA kept the wheel rotating for a longer time compared to controls, traveling a significantly longer total distance (Table 6). This result indicates that the dose of ABA taken with the glucose improves muscle performance increasing resistance to physical exertion. In addition, also the maximal speed recorded was 3.2 times higher compared with that of the controls. It is noteworthy that there was no coercion to use the wheel; thus, this test measured the spontaneous physical activity of the animals in the absence of preliminary training.

The improvement of muscle performance, i.e. of the contractile function of skeletal muscle, observed in mice chronically treated with ABA 1 µg/Kg was not obvious from the increased glucose transport reported in myoblasts incubated in vitro with 100 nM ABA, reported in the literature (Bruzzone S. et al. 2012). Indeed, the myoblasts used in the study by Bruzzone et al., together with adipocytes, as a model cell system expressing the glucose transporter GLUT4 are immature cells, structurally, metabolically and functionally very different from the mature muscle cells present in skeletal muscle: e.g. myoblasts are unable to contract. The improved muscle performance compared to the controls of the mice chronically treated with ABA 1 µg/Kg described here by the inventors certainly depends on more complex metabolic modifications induced by ABA in skeletal muscle, such as an increased availability of glycogen and/or ATP during contractile activity.

TABLE 6

Daily oral intake of synthetic ABA at a dose of 1 µg/Kg improves muscle performance in mice. Male CD1 mice (outbred) (8/group) with a mean weight of 45.1 and 43.3 g for animals treated with glucose and glucose + ABA, respectively, were kept for the same time (12 hours) in two cages, each containing a wheel connected to a digital cyclometer, capable of measuring the total distance travelled and the duration of rotation of the wheel. The tests (n = 2 for each group of animals) were performed during the night hours, with ad libitum food and water, containing glucose (controls) or glucose + ABA.

|  | Time of use (min) | Total distance covered (m) |
|---|---|---|
| glucose | 46 | 1625 |
| glucose + ABA | 105 | 2693 |

Stability Tests of ABA at High Temperatures

Experiments were performed to evaluate the heat stability of synthetic ABA or of ABA naturally present in aqueous and supercritical extracts. Samples containing known nanomolar concentrations of ABA (either synthetic or present in the extracts) were divided into two aliquots of equal volume and subjected or not (control) to autoclave sterilization at 121° C. for 8 min (the condition generally applied to the sterilization of food). After sterilization, 100 µl of each aliquot and its un-sterilized control were injected into an analytical Hypercarb column (Thermo Scientific, Pittsburgh, Pa.) (4.6×100 mm; particle size 5 µm). Solvent A was water containing 0.1% formic acid (FOA), solvent B was acetonitrile containing 0.1% FOA and solvent flux was 0.8 ml/min. The linear elution gradient was from 100% A to 100% B in 30 min. Fractions were taken every 30 sec, lyophilized, re-dissolved in 11 µl of a solution composed of 90% solvent A and 10% solvent B of the HPLC-coupled mass spectrometry analysis and [$^2$H6]-ABA was added as an internal standard. Samples were analyzed as previously described under "Determination of the ABA content in several foods". The amount of ABA present in the aliquots subjected to sterilization was unchanged compared with that measured in the control samples.

Nutraceutical Compositions Containing ABA

The amount of ABA and/or of conjugates thereof capable of being hydrolyzed in vivo, present in a food serving or in a nutraceutical composition, such as to yield a dose of ABA and/or of its conjugates comprised in the dose-range described in this invention, is approx. 100 µg. The following are explanatory, but not limitative examples, of some types of food or nutraceutical compositions to which ABA, or ABA-conjugates, synthetic or extracted from vegetal sources, can be added to improve the metabolic utilization of sugars. Vegetal extracts rich in ABA are for instance aqueous or supercritical extracts of apricots, bilberry or grape seed, in liquid phase or lyophilized.

Diet food for:
athletes (energizing drinks, energizing bars, dietary integrators);
normoglycemic subjects (bakery products; jam; chocolate, spreadable and not; honey; desserts)
diabetic subjects (bread, pasta, bakery products, desserts).

Examples of liquid servings are: a 330-ml can, a 250-ml Tetra Pak, a 200-ml Brik.

Examples of solid servings are: ready-made servings (e.g. Twinkies, snacks, chocolate confectionary, etc.) or servings expressly indicated on the packing of the food (e.g. jar of spreadable chocolate, jar of jam, biscuit bags, etc.).

Experiments performed both on synthetic ABA and on ABA naturally present in aqueous and supercritical extracts demonstrated that the molecule is unmodified (as determined by HPLC-MS) after high-temperature (121° C.) sterilization procedures usually employed for food and beverages before commercialization.

Examples of nutraceutical compositions to which the dehydrated powder of the above-mentioned vegetal extracts can be added are commercially available dietary supplements. The following are explanatory, but not limitative examples of some types of dietary supplements: probiotics, salts, macro- and micro-nutrients.

Further examples of products included in the scope of the present invention are health products, foods for special medical purposes and special dietary foods, the purpose and use of which are known to the expert in the field.

BIBLIOGRAPHY

Bassaganya-Riera J., Guri A. J., Hontecillas R., US2007/0184060 A1.
Bruzzone S., Ameri P., Briatore L., Mannino E., Basile G., Andraghetti G., Grozio A., Magnone M., Guida L., Scarff S., Salis A., Damonte G., Sturla L., Nencioni A., Fenoglio D., Fiory F., Miele C., Beguinot F., Ruvolo V., Bormioli M., Colombo G., Maggi D., Murialdo G., Cordera R., De Flora A., Zocchi E. FASEB J. 26(3):1251-60, 2012.
Bruzzone S., Moreschi I., Usai C., Guida L., Damonte G., Salis A., Scarff S., Millo E., De Flora A., Zocchi E. Proc Natl Acad Sci USA 104(14):5759-64, 2007.
Bruzzone, S., Bodrato N., Usai C., Guida L., Moreschi I., Nano R., Antonioli B., Fruscione F., Magnone M., Scarff S., De Flora A., Zocchi E. J. Biol. Chem. 283(47):32188-97, 2008.
Fiume R., Ramazzotti G., Faenza I., Piazzi M., Bavelloni A., Billi A. M., Cocco L. FASEB J. 26(1):203-10, 2012.
Guri A. J., Hontecillas R., Si H., Liu D. and Bassaganya-Riera J. Clin Nutr 26:107-116, 2007
Jiang F., Hartung W. J Exp Bot 59: 37-43, 2008.
Ledford H. Nature 504: 198, 2013
Lee K. H., Piao H. L., Kim H. Y., Choi S. M., Jang F., Hartung W., Hwang I., Kwak J. M., Lee I. J., Hwang I. Cell 126(6):1109-20, 2006.
Lin Y. e Sun Z. J. Endocrinology 204: 1-18, 2010.
Magnone M., Bruzzone S., Guida L., Damonte G., Millo E., Scarff S., Usai C., Palombo D., De Flora A., Zocchi E. J. Biol. Chem. 284(26):17808-18, 2009.
Scarff S., Ferraris C., Fruscione F., Fresia C., Guida L., Bruzzone S., Usai C., Parodi A., Millo E., Salis A., Burastero G., De Flora A., Zocchi E. Stem Cells 26(11):2855-64, 2008.
Tschope D., Hanefeld M., Meier J., Gitt A., Halle M., Bramlage P e Schumm-Draeger P-A. Cardiovascular Diabetology 12: 62-71, 2013.

The invention claimed is:

1. A method for therapeutically treating, or controlling hyperglycemia in a subject in need thereof, without an increase in insulinemia, said method comprising
orally administering to said subject an effective amount of abscisic acid (ABA) or an in vivo hydrolyzable ABA-conjugate at a dose of between 0.15 and 95 µg/day per Kg of body weight of said subject.

2. The method according to claim 1, wherein said dosage form is in a food product further comprising organic and/or inorganic substances,
said food product being selected from the group consisting of carbohydrate-containing human or animal food, healthy products, supplements, sugar-containing energizing beverages and nutraceutical compositions.

3. The method according to claim 1, wherein said dose is between 0.5 and 50 µg/day per Kg of body weight of said subject.

4. The method according to claim 1, wherein said dose is between 1 and 10 µg/day per Kg of body weight of said subject.

5. The method according to claim 1, wherein said subject is a human or an animal.

6. The method according to claim 5, wherein said subject is a healthy, diabetic or pre-diabetic subject.

7. The method according to claim 1, wherein said method comprises one of the following:
improving glucose tolerance without increasing insulin secretion;
improving muscle performance and/or endurance;
reducing insulin secretion in response to glucose intake;
reducing insulin-dependent triglycerides synthesis and accumulation thereof, with a resulting improved weight control after carbohydrate intake.

8. The method according to claim 1, wherein said in vivo hydrolysable ABA-conjugate is a conjugate of ABA with a compound selected from the group consisting of organic acids, inorganic acids, primary alcohols, secondary alcohols, tertiary alcohols, monosaccharides, disaccharides, polysaccharides, biogenic amines and amino acids.

9. A method for therapeutically treating, or controlling hyperglycemia in a subject in need thereof, without an increase in insulinemia, said method comprising
orally administering to said subject an effective amount of abscisic acid (ABA) or an in vivo hydrolyzable ABA-conjugate at a dose of between 0.15 and 95 µg/day per Kg of body weight of said subject,
wherein said effective amount of abscisic acid (ABA) or of an in vivo hydrolyzable ABA-conjugate is in the form of a dosage form adapted for oral administration of said ABA or said ABA-conjugate at a daily dose of between 0.45 µg and 11.4 mg.

10. The method according to claim 9, wherein said dose is between 1.5 µg and 6 mg.

11. The method according to claim 9, wherein said dose is between 3 µg and 1.2 mg.

12. The method according to claim 9, wherein said abscisic acid (ABA) or said ABA-conjugated is contained in a plant extract.

13. The method according to claim 9, wherein said ABA-conjugate is hydrolysable in vivo by hydrolysis of an anhydride, an ester or an amide bond.

14. The method according to claim 13, wherein said in vivo hydrolysable ABA-conjugate is a conjugate of ABA with a compound selected from the group consisting of organic acids, inorganic acids, primary alcohols, secondary alcohols, tertiary alcohols, monosaccharides, disaccharides, polysaccharides, biogenic amines and amino acids.

15. The method according to claim 14, wherein said in vivo hydrolysable ABA-conjugate is ABA-glucosyl ester (ABA-GE).

* * * * *